(12) United States Patent
Mori et al.

(10) Patent No.: US 8,368,028 B2
(45) Date of Patent: Feb. 5, 2013

(54) SOLID-STATE IMAGE PICKUP DEVICE

(75) Inventors: Harumichi Mori, Hamamatsu (JP);
Ryuji Kyushima, Hamamatsu (JP);
Kazuki Fujita, Hamamatsu (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 54 days.

(21) Appl. No.: 12/999,188

(22) PCT Filed: Jun. 11, 2009

(86) PCT No.: PCT/JP2009/060697
§ 371 (c)(1),
(2), (4) Date: Feb. 10, 2011

(87) PCT Pub. No.: WO2009/154136
PCT Pub. Date: Dec. 23, 2009

(65) Prior Publication Data
US 2011/0135057 A1    Jun. 9, 2011

(30) Foreign Application Priority Data

Jun. 18, 2008   (JP) ................................ P2008-159363

(51) Int. Cl.
*G01T 1/24*   (2006.01)
(52) U.S. Cl. .................................... 250/370.09; 378/62
(58) Field of Classification Search .............. 250/370.09
See application file for complete search history.

(56) References Cited

U.S. PATENT DOCUMENTS

| 5,693,948 | A * | 12/1997 | Sayed et al. | 250/370.09 |
| 2003/0164888 | A1 * | 9/2003 | Orava et al. | 348/308 |
| 2004/0202281 | A1 * | 10/2004 | Colbeth et al. | 378/98.8 |
| 2005/0151873 | A1 * | 7/2005 | Murakami | 348/340 |
| 2007/0216564 | A1 | 9/2007 | Koseki | |

FOREIGN PATENT DOCUMENTS

| JP | 7-209430 | 8/1995 |
| JP | 2000-32357 | 1/2000 |
| JP | 2002-344809 | 11/2002 |
| JP | 2004-208754 | 7/2004 |
| JP | 2006-521716 | 9/2006 |
| JP | 3897357 | 1/2007 |
| JP | 2008-17019 | 1/2008 |
| WO | 2005/109037 | 11/2005 |

\* cited by examiner

*Primary Examiner* — Marcus Taningco
(74) *Attorney, Agent, or Firm* — Drinker Biddle & Reath LLP

(57) ABSTRACT

A solid-state image pickup device 1 includes a semiconductor substrate 3A having a pixel array 10A with pixels arrayed in M rows and NA columns, a semiconductor substrate 3B having a pixel array 10B with pixels arrayed in M rows and NB columns, and a first column of which is arranged along an NA-th column of the pixel array 10A, and a signal output section 20. The signal output section 20 outputs digital values corresponding to the respective columns from the first column to the n-th column ($2 \leq n < NA$) of the pixel array 10A, sequentially from the n-th column to the first column, and in parallel with this output, outputs digital values corresponding to the respective columns from the (n+1)-th column of the pixel array 10A to the NB-th column of the pixel array 10B, sequentially in a reverse order to that of the first column to the n-th column of the pixel array 10A. Thus, the time required for imaging of one frame is reduced in the solid-state image pickup device with a configuration where pixel arrays formed on two substrates are tiled in their row direction.

4 Claims, 16 Drawing Sheets

Fig.4
(a)
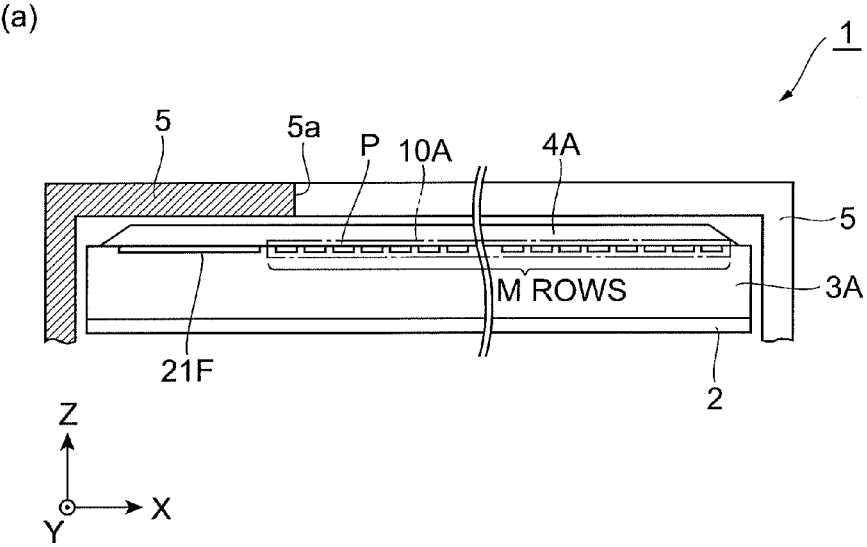
(b)
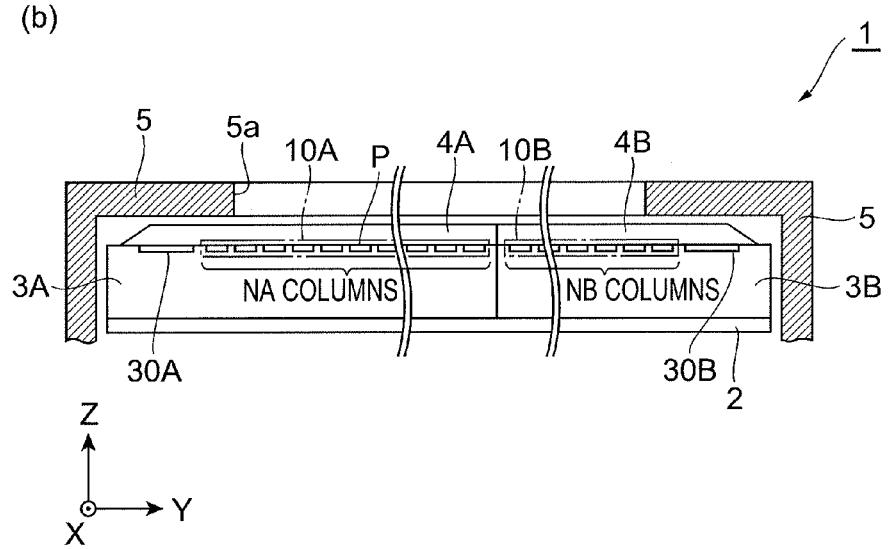

Fig.11
(a)
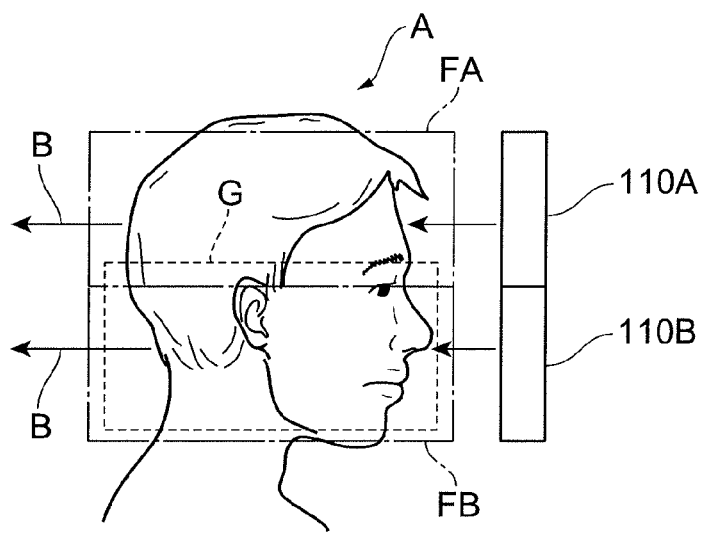
(b)
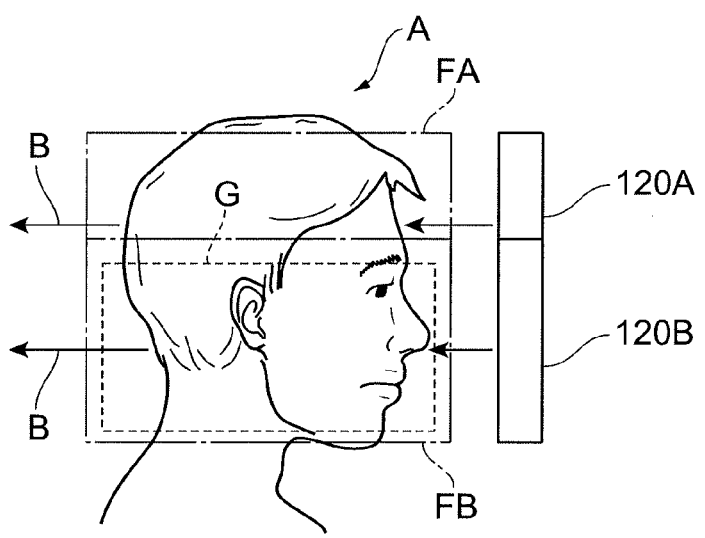

Fig.12
(a)
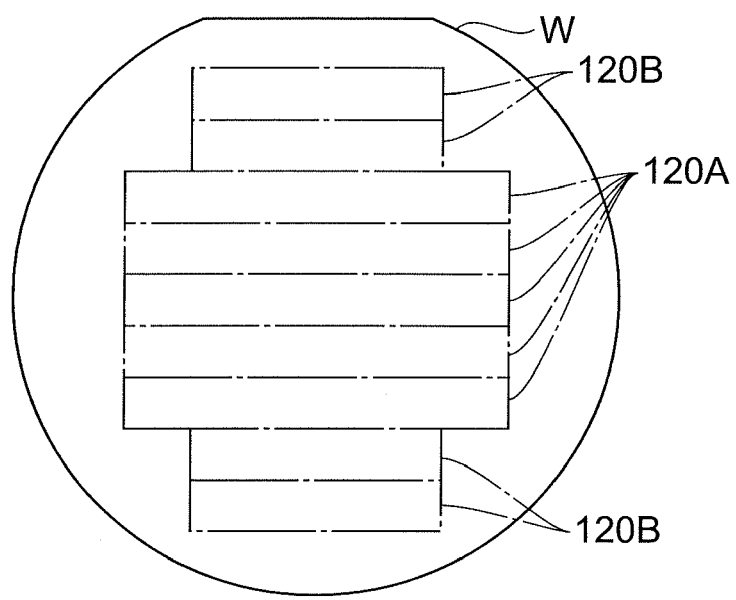
(b)
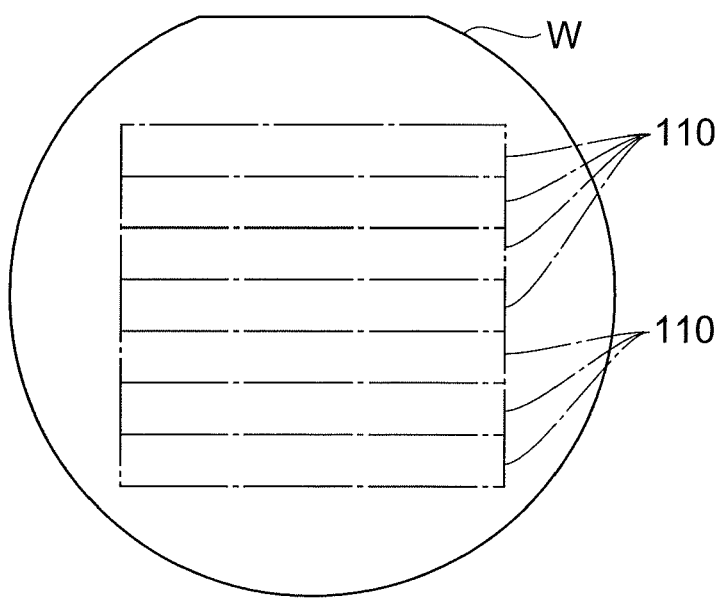

Fig.16
(a) 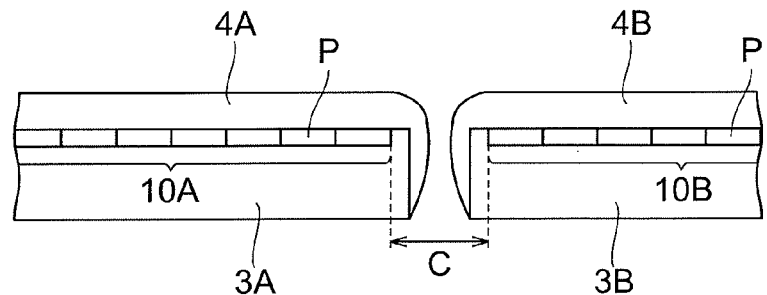
(b) 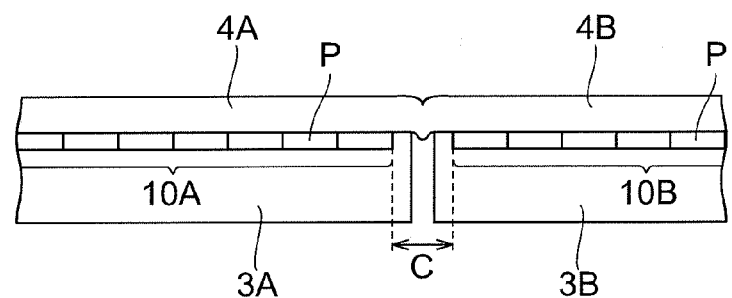
(c) 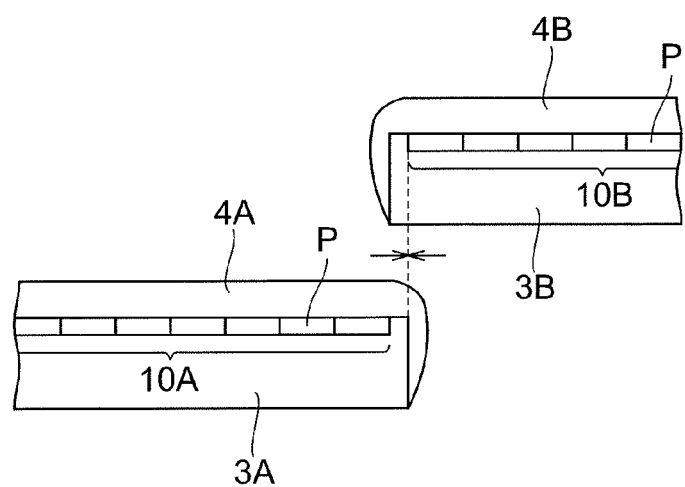

SOLID-STATE IMAGE PICKUP DEVICE

TECHNICAL FIELD

The present invention relates to a solid-state image pickup device for generating image data according to an incident X-ray image.

BACKGROUND ART

In radiographic technology, X-ray imaging systems using solid-state image pickup elements in place of X-ray sensitive films have come to be widely used in recent years. Such X-ray imaging systems are more convenient such as allowing confirming X-ray images in real time without the necessity for development as in X-ray sensitive films, and have a point of superiority also in the aspect of the storage stability of data and ease in handling. For example, also in X-ray photography for dental diagnosis, such X-ray imaging systems have spread in various imaging modes such as panoramic mode, cephalometric mode, and CT. As an example, a dental X-ray apparatus disclosed in Patent Document 1 images X-rays having been output from an X-ray source and transmitted through a subject, by an X-ray detecting element of a CCD type.

Moreover, as solid-state image pickup devices to be used for such X-ray imaging systems, ones using CMOS technology are known, and among these, a passive pixel sensor (PPS) type device is known. The PPS type solid-state image pickup device includes a pixel array where PPS type pixels including photodiodes for generating charges of amounts according to incident light intensities are two-dimensionally arranged in M rows and N columns, converts a charge generated in the photodiode in response to light incidence in each pixel to a voltage value in an integration circuit, and further converts this voltage value to a digital value to be output.

Generally, an output terminal of each of the M pixels of each column is connected, via a readout wiring line provided corresponding to the column, with an input terminal of an integration circuit provided corresponding to the column. And, charges generated in the photodiodes of the respective pixels are, in sequence from the first row to the M-th row and row by row, input to the integration circuit through the readout wiring line corresponding to the column, and a voltage value according to the charge amount is input from the integration circuit to an analog/digital converter in sequence from the first column to the N-th column.

Citation List

Patent Literature

Patent Document 1: Japanese Patent Application Laid-Open No. 2004-208754

SUMMARY OF INVENTION

Technical Problem

In the foregoing X-ray imaging system, the size required for the pixel array of the solid-state image pickup device varies depending on its imaging application, and in, for example, radiography for dental diagnosis, a long solid-state image pickup device whose pixel array has a longitudinal width of 22 cm or more is required in cephalometric radiography. When such a long solid-state image pickup device is required, it may be difficult, depending on the diameter of a semiconductor wafer to be used for production of the solid-state image pickup device, to prepare the solid-state image pickup device on a single substrate. In such a case, the required size can be satisfied by arranging two substrates shorter than the size required for a solid-state image pickup device side by side in the long-length direction, and aligning their respective pixel arrays with each other to be used as one solid-state image pickup device (so-called tiling).

However, because it is difficult in manufacturing to eliminate a gap between an end portion of a substrate and an end portion of a pixel array to be prepared on the substrate, when two substrates arranged side by side are used, a region (dead area) where no X-ray image is taken is generated at a boundary portion (seam) between pixel arrays of these. Depending on the imaging application, such a dead area may be limited in position. For example, in dental cephalography, where the solid-state image pickup device is moved laterally (horizontal direction) with its long-length direction made coincident with the up-and-down direction (vertical direction) while imaging is performed, because a temporomandibular joint exists near the center of an X-ray image, image data on a diagnostically important part may be lacking if the dead area exists near the center of a tiled pixel array as a whole. Therefore, in such a case, it becomes necessary to shift the position of the dead area from near the center by differentiating the pixel arrays in the two substrates in longitudinal width from each other.

Here, when the two substrates to form the above-described PPS type solid-state image pickup device are arranged side by side in the row direction of their pixel arrays, the pixel arrays of the respective substrates being different in width in the long-length direction from each other result in a difference in the number of columns of the pixel arrays of the respective substrates from each other, so that the following problem occurs. That is, when the PPS type solid-state image pickup device, in which a charge generated in the photodiode of each pixel is converted column by column to a voltage value, and further converted to a digital value, outputs the digital values in parallel from the two substrates, the time required for completing output of digital values of all columns is different between the substrates, and the substrate with a smaller number of columns can only be placed in a waiting state for the time until completing output of digital values from the substrate with a larger number of columns, so that the time required for imaging of one frame becomes long.

The present invention has been made in order to solve the above-described problem, and an object thereof is, in a solid-state image pickup device with a configuration where pixel arrays formed on two substrates are tiled in their row direction, to reduce the time required for imaging of one frame.

Solution to Problem

A solid-state image pickup device according to the present invention is a solid-state image pickup device for generating image data according to an incident X-ray image, and comprises: a first substrate having a first pixel array with M×NA (M and NA are each an integer not less than 2) pixels each including a photodiode that are two-dimensionally arrayed in M rows and NA columns; a second substrate having a second pixel array with M×NB (NB is an integer not less than 2 and smaller than NA) pixels each including a photodiode that are two-dimensionally arrayed in M rows and NB columns, and a first column of which is arranged along an NA-th column of the first pixel array; (NA+NB) readout wiring lines disposed for each column of the first and second pixel arrays, and each connected to the photodiode included in the pixel of a corresponding column via a readout switch; a signal output section for holding a voltage value according to an amount of charge input through the readout wiring line, and outputting the held voltage value converted to a digital value by one or a plurality of analog/digital converters; and a scintillator for generating scintillation light in response to incident X-rays to convert the X-ray image into an optical image, and outputting the optical image to the first and second pixel arrays, in which one or a plurality of consecutive columns including a first column of the first pixel array and one or a plurality of consecutive columns including an NB-th column of the second pixel array serve as a non-sensitive region shielded from incident X-rays, and the signal output section outputs the digital values corresponding to the respective columns from the first column to an n-th column ($2 \leq n < NA$) of the first pixel array, sequentially starting from the first column to the n-th column, or starting from the n-th column to the first column, and in parallel with this output, outputs the digital values corresponding to the respective columns from an (n+1)-th column of the first pixel array through the NA-th column and the first column of the second pixel array to the NB-th column, sequentially in a reverse order to that of the first column to the n-th column of the first pixel array.

In the solid-state image pickup device according to the present invention, the first substrate having the first pixel array and the second substrate having the second pixel array smaller in the number of columns than the first pixel array are tiled so that the NA-th column of the first pixel array and the first column of the second pixel array lie along each other. That is, this solid-state image pickup device has a pixel array of (NA+NB) columns where the first column to the NB (<NA)-th column of the second pixel array are added to the first column to the NA-th column of the first pixel array.

Then, the signal output section, when outputting digital values to a data bus or the like, outputs in parallel the digital values corresponding to the respective columns on and before the n-th column (that is, from the first column to the n-th column) of the first pixel array and the digital values corresponding to the respective columns on and after the (n+1)-th column and the first column to the NB-th column of the second pixel array (that is, from the (n+1)-th column of the first pixel array through the NA-th column and the first column of the second pixel array to the NB-th column). By thus dividing an output operation at a boundary of the column (the n-th column) between the first column and the NA-th column of the first pixel array with a larger number of columns to output digital values in parallel, the number of columns in one divided region and the number of columns in the other divided region can be equalized or approximated to each other in the number of columns. Therefore, by the solid-state image pickup device according to the present invention, as compared to, for example, a configuration for outputting digital values from the first column to the NA-th column of the first pixel array and outputting in parallel therewith digital values from the first column to the NB-th column of the second pixel array, the wait time in an output operation can be approximated to zero, so that the time required for imaging of one frame can be effectively reduced.

Moreover, in the solid-state image pickup device according to the present invention, one or a plurality of consecutive columns including the first column of the first pixel array and one or a plurality of consecutive columns including the NB-th column of the second pixel array serve as a non-sensitive region shielded from incident X-rays. In a solid-state image pickup device for generating image data according to an incident X-ray image, it is often the case that a pixel array is surrounded by an X-ray shielding member in order to protect a circuit part such as a shift register arranged aside the pixel array from X-rays. In addition, if the X-ray shielding member hangs over a part of the pixel array, the non-sensitive region described above is produced in the pixel array. Of the digital values to be output from the signal output section, digital values corresponding to pixels included in this non-sensitive region result in invalid data not relevant to the X-ray image.

In such a case, if the output order of digital values in one region divided at a boundary of the n-th column and the output order of digital values in the other region are the same order, the following disadvantage occurs. That is, the digital values output from the signal output section are output to another electronic circuit (such as a CPU) via a data bus or the like, but at this time, the digital values (invalid data) corresponding to the non-sensitive region are output first from one region, and the invalid data is output last from the other region. If the position of the invalid data in the output order of digital values is different between the regions as such, this can be a barrier when performing real-time processing in another electronic circuit.

To cope with such problems simultaneously, in the solid-state image pickup device according to the present invention, the output order of digital values in one region divided at the boundary of the n-th column and the output order of digital values in the other region are reverse to each other. That is, the signal output section outputs digital values corresponding to the respective columns from the first column to the n-th column of the first pixel array, sequentially starting from the first column up until the n-th column, or starting from the n-th column up until the first column, and outputs digital values corresponding to the respective columns from the (n+1)-th column of the first pixel array through the NA-th column and the first column of the second pixel array to the NB-th column, sequentially in a reverse order to that of the first column to the n-th column of the first pixel array. As a result of the signal output section outputting digital values in such an order to a data bus or the like, the position of invalid data in the output order of digital values can be made coincident between the regions, which allows easily performing real-time processing in another electronic circuit.

Advantageous Effects of Invention

According to the present invention, in a solid-state image pickup device with a configuration where pixel arrays formed on two substrates are tiled in their row direction, the time required for imaging of one frame can be reduced.

BRIEF DESCRIPTION OF DRAWINGS

FIG. 4 includes (a) a side sectional view of the solid-state image pickup device 1 along a line IVa-IVa in FIG. 3, and (b) a side sectional view of the solid-state image pickup device 1 along a line IVb-IVb in FIG. 3.

FIG. 11 includes (a) a view showing a state where two pixel arrays 110A, 110B are tiled in the up-and-down direction to move in parallel in the horizontal direction while performing imaging, and (b) a view showing a state where two pixel arrays 120A, 120B are tiled in the up-and-down direction to move in parallel in the horizontal direction while performing imaging.

FIG. 12 includes (a) a view showing a state where a plurality of pixel arrays 120A that are wider in long-length direction width and a plurality of pixel arrays 120B that are narrower in long-length direction width are imposed in a silicon wafer W, and (b) a view showing a state where a plurality of pixel arrays 110 that are equal in long-length direction width are imposed in a silicon wafer W.

FIG. 16 includes (a) a view showing a method for arranging semiconductor substrates 3A, 3B vapor-deposited with film-like scintillators 4A, 4B on their surfaces, respectively, adjacent to each other on the same plane, (b) a view showing a method for arranging semiconductor substrates 3A, 3B adjacent to each other on the same plane, and vapor-depositing scintillators 4A, 4B in a lump after the semiconductor substrates 3A, 3B are arranged, and (c) a view showing a method for arranging semiconductor substrates 3A, 3B so that an end portion of the semiconductor substrate 3B is overlapped with an end portion of the semiconductor substrate 3A.

DESCRIPTION OF EMBODIMENTS

Hereinafter, embodiments of the present invention will be described in detail with reference to the accompanying drawings. Also, the same components will be denoted with the same reference symbols in the description of the drawings, and overlapping description will be omitted.

Figure 1:
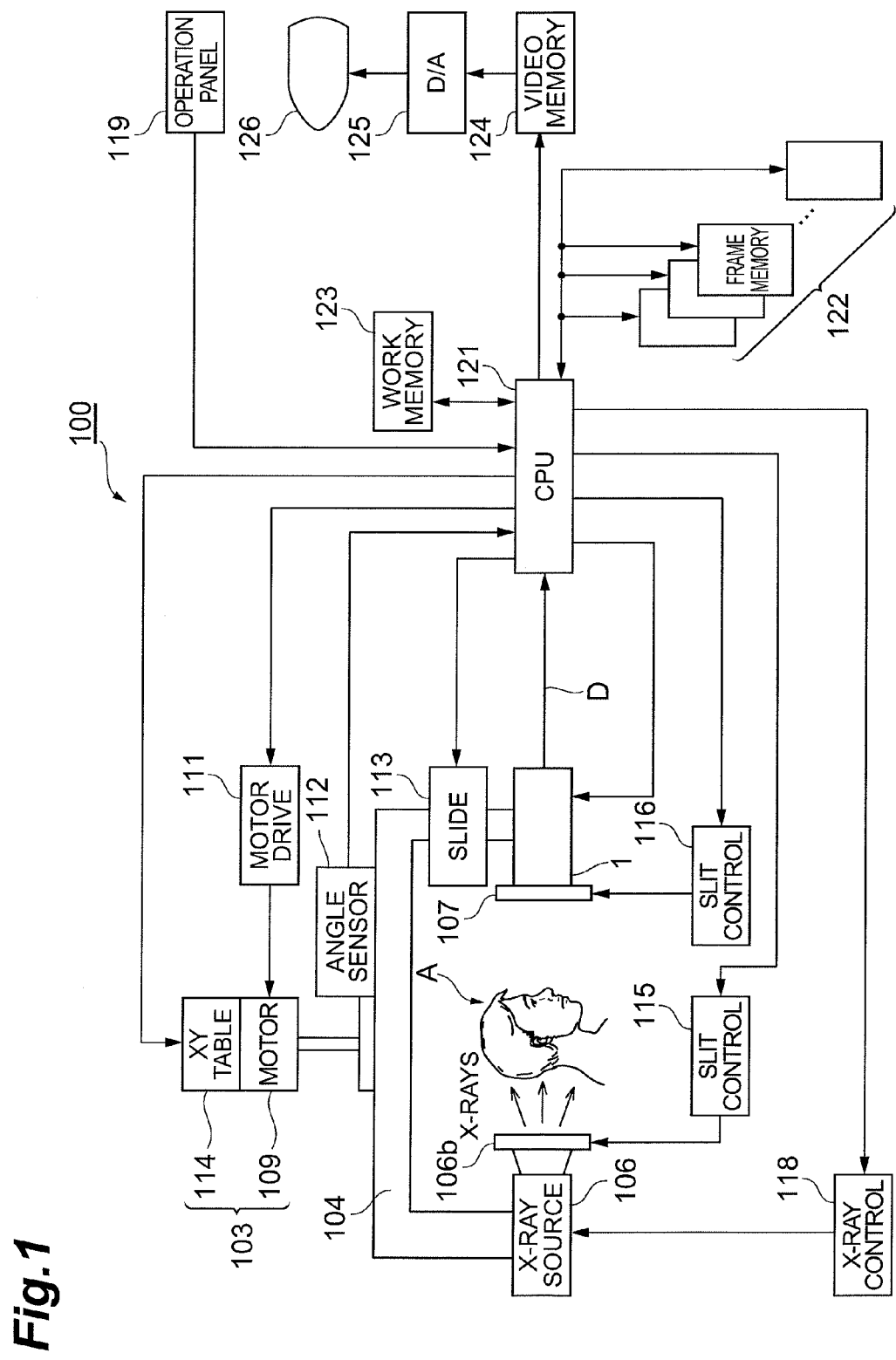
FIG. 1 is a configuration diagram of an X-ray imaging system 100.

FIG. 1 is a diagram showing a configuration of a medical X-ray imaging system 100 including a solid-state image pickup device 1 according to an embodiment of the present invention. The X-ray imaging system 100 of the present embodiment mainly has imaging modes such as panoramic radiography, cephalometric radiography, and CT in dentistry medical treatment, and takes an X-ray image of a jaw of a subject under test. The X-ray imaging system 100 includes the solid-state image pickup device 1 and an X-ray generating device 106, and images X-rays having been output from the X-ray generating device 106 and transmitted through a subject A (that is, the jaw of the subject under test) by means of the solid-state image pickup device 1.

The X-ray generating device 106 generates X-rays toward the subject A. The radiation field of X-rays generated from the X-ray generating device 106 is controlled by a primary slit plate 106b. The X-ray generating device 106 has an X-ray tube built therein, and by adjusting conditions of the X-ray tube, such as a tube voltage, a tube current, and energization time, the X-ray dose to the subject A is controlled. Moreover, the X-ray generating device 106 can, as a result of the opening range of the primary slit plate 106b being controlled, output X-rays at a predetermined divergence angle when in one imaging mode, and output X-rays at a narrower divergence angle than the predetermined divergence angle when in another output mode.

The solid-state image pickup device 1 is a CMOS type solid-state image pickup device having a plurality of pixels arrayed two-dimensionally, and converts an X-ray image transmitted through the subject A into electrical image data D. In front of the solid-state image pickup device 1, a secondary slit plate 107 that limits an X-ray incident region is provided.

The X-ray imaging system 100 further includes a swing arm 104. The swing arm 104 holds the X-ray generating device 106 and the solid-state image pickup device 1 so as to be opposed to each other, and swings these around the subject A in CT and panoramic radiography. Moreover, in the case of cephalography and linear tomography, a slide mechanism 113 for linearly displacing the solid-state image pickup device 1 and the X-ray generating device 106 with respect to the subject A is provided. The swing arm 104 is driven by an arm motor 109 that forms a rotary table, and a rotation angle thereof is detected by an angle sensor 112. Moreover, the arm motor 109 is mounted on a movable portion of an XY table 114, and the center of rotation is arbitrarily adjusted in a horizontal plane.

The image data D output from the solid-state image pickup device 1 is once taken in a CPU (central processing unit) 121, and thereafter stored in a frame memory 122. From the image data stored in the frame memory 122, a tomographic image along any tomographic plane, a panoramic image, a cephalometric image, and the like are reproduced by a predetermined arithmetic processing. These reproduced images are output to a video memory 124, and converted to analog signals by a D/A converter 125, and then displayed by an image display section 126 such as a CRT (cathode ray tube), and provided for various diagnoses.

The CPU 121 is connected with a work memory 123 required for signal processing, and further connected with an operation panel 119 having a panel switch, an X-ray irradiation switch, etc. Moreover, the CPU 121 is connected to a motor drive circuit 111 that drives the arm motor 109, slit control circuits 115 and 116 that control the opening ranges of the primary slit plate 106b and the secondary slit plate 107, an X-ray control circuit 118 that controls the X-ray generating device 106, respectively, and further outputs a clock signal to drive the solid-state image pickup device 1. The X-ray control circuit 118 feedback-controls the X-ray dose to the subject based on signals imaged by the solid-state image pickup device 1.

Figure 2:
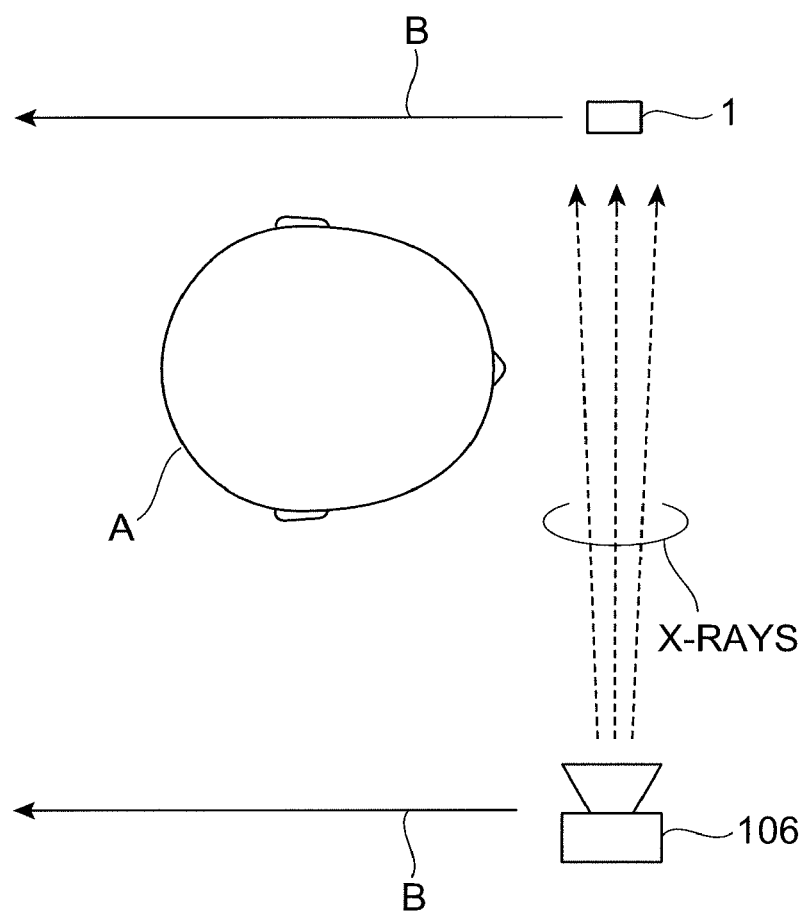
FIG. 2 is a view showing a state where a solid-state image pickup device 1 and an X-ray generating device 106 are linearly displaced with respect to a subject A (head of a subject under test), observed from upside of the subject A.

FIG. 2 is a view showing a state where the solid-state image pickup device 1 and the X-ray generating device 106 are linearly displaced with respect to the subject A (head of a subject under test), observed from upside of the subject A. In the case of cephalography, the solid-state image pickup device 1 and the X-ray generating device 106 maintained opposed to each other at both sides across the subject A linearly move in the same direction (arrow B in the figure) by the slide mechanism 113, while irradiating the subject A with X-rays, and continuously performs imaging of X-ray images transmitted through the subject A.

Figure 3:
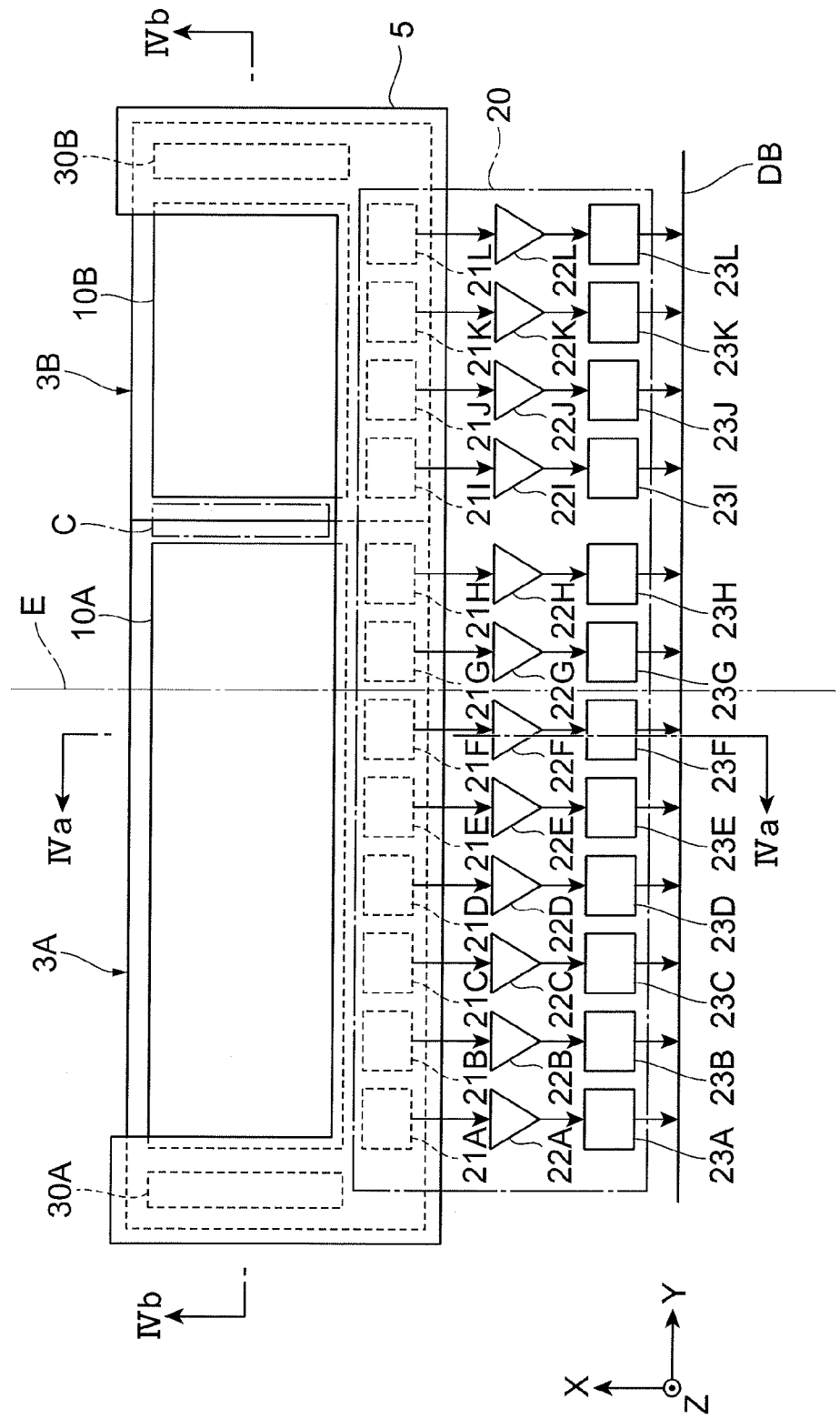
FIG. 3 is a plan view of the solid-state image pickup device 1.

FIG. 3 and FIG. 4 are views showing a configuration of the solid-state image pickup device 1 in the present embodiment. FIG. 3 is a plan view of the solid-state image pickup device 1. (a) in FIG. 4 is a side sectional view of the solid-state image pickup device 1 along a line IVa-IVa in FIG. 3, and (b) in FIG. 4 is a side sectional view of the solid-state image pickup device 1 along a line IVb-IVb in FIG. 3. Here, in FIG. 3 and FIG. 4, an XYZ orthogonal coordinate system is also shown for easy understanding.

As shown in FIG. 3 and FIG. 4(*a*), the solid-state image pickup device 1 includes a semiconductor substrate 3A (first substrate) and a semiconductor substrate 3B (second substrate), and these two semiconductor substrates 3A, 3B compose one imaging region. The size required for the imaging region of the solid-state image pickup device 1 varies depending on its imaging application, but in X-ray photography for dental diagnosis, a long one whose imaging region has a longitudinal width of 22 cm or more is required in cephalography. Therefore, as in the present embodiment, the required size can be satisfied by arranging the two semiconductor substrates 3A, 3B shorter than the size required for the solid-state image pickup device 1 side by side in the long-length direction, and aligning their respective pixel arrays 10A, 10B with each other to be used as one imaging region (so-called tiling). Here, when two semiconductor substrates 3A, 3B arranged side by side are used as such, a region (dead area C) where no X-ray image is taken is produced at a boundary portion (seam) between pixel arrays of these. This is because it is difficult in manufacturing to eliminate a gap between an end portion of each of the semiconductor substrates 3A and 3B and an end portion of each of the pixel arrays 10A, 10B to be prepared on these semiconductor substrates 3A, 3B.

The solid-state image pickup device 1 includes the pixel array 10A (first pixel array) and a scan shift register 30A respectively formed on a main surface of the semiconductor substrate 3A and the pixel array 10B (second pixel array) and a scan shift register 30B respectively formed on a main surface of the semiconductor substrate 3B. Moreover, the solid-state image pickup device 1 further includes a signal output section 20, and this signal output section 20 has a plurality of signal readout sections 21A to 21H formed on the main surface of the semiconductor substrate 3A, a plurality of signal readout sections 21I to 21L formed on the main surface of the semiconductor substrate 3B, a plurality of analog/digital (A/D) converters 22A to 22L corresponding to the respective signal readout sections 21A to 21L, and a plurality of FIFO (First-In-First-Out) data buffers 23A to 23L corresponding to the respective A/D converters 22A to 22L.

Moreover, the solid-state image pickup device 1 includes a flat plate-like base member 2, scintillators 4A, 4B, and an X-ray shielding member 5. The above-described semiconductor substrates 3A, 3B are attached to the base member 2, and the scintillators 4A and 4B are arranged on the semiconductor substrate 3A and on the semiconductor substrate 3B, respectively. The scintillators 4A and 4B generate scintillation light in response to incident X-rays to convert X-ray images into optical images, and output these optical images to the pixel arrays 10A and 10B, respectively. The scintillators 4A and 4B are installed so as to cover the pixel arrays 10A, 10B, respectively, or provided by vapor deposition on the pixel arrays 10A, 10B, respectively. The X-ray shielding member 5 is made of a material such as lead having an extremely low X-ray transmittance. The X-ray shielding member 5 covers a peripheral portion of the semiconductor substrates 3A, 3B, particularly a region where the scan shift registers 30A, 30B and the signal readout sections 21A to 21L are arranged, and prevents X-rays from entering the scan shift registers 30A, 30B and the signal readout sections 21A to 21L.

The pixel array 10A is composed of M×NA pixels P (refer to (a), (b) in FIG. 4) two-dimensionally arrayed in M rows and NA columns. Moreover, the pixel array 10B is composed of M×NB pixels P two-dimensionally arrayed in M rows and NB columns. Also, in FIG. 3, the column direction is coincident with the X-axis direction, and the row direction is coincident with the Y-axis direction. M, NA, and NB are each an integer not less than 2, and satisfy NA>NB. Moreover, the number of pixels P (NA+NB) in the row direction in the pixel arrays 10A, 10B is preferably larger than M, the number of pixels P in the column direction. In such a case, the imaging region consisting of the pixel arrays 10A and 10B exhibits a rectangular shape taking the row direction (Y-axis direction) as its long-length direction and taking the column direction (X-axis direction) as its short-length direction. The pixels P are arrayed at a pitch of, for example, 100 μm, are pixels of the PPS type, and have a common configuration.

Here, in FIG. 3, a column located at the leftmost end out of the NA columns contained in the pixel array 10A (that is, a column with the minimum y-coordinate) is provided as a first column, and a column located at the opposite right end is provided as an NA-th column. Moreover, in the same figure, a column located at the leftmost end out of the NB columns contained in the pixel array 10B (a column with the minimum y-coordinate) is provided as a first column, and a column located at the opposite right end is provided as an NB-th column. In this case, the pixel arrays 10A and 10B are arranged in the present embodiment so that the first column of the pixel array 10B and the NA-th column of the pixel array 10A lie along each other.

Moreover, one or a plurality of consecutive columns including the first column of the pixel array 10A are covered with the X-ray shielding member 5, and serve as a non-sensitive region shielded from incident X-rays. That is, these columns, into which no light is made incident and from which no charge is generated, thus do not contribute to imaging. Similarly, one or a plurality of consecutive columns including the NB-th column of the pixel array 10B are also covered with the X-ray shielding member 5, and serve as a non-sensitive region. Therefore, in the pixel arrays 10A and 10B, an effective region for imaging is configured by other pixel columns excluding these pixel columns covered with the X-ray shielding member 5. In other words, the effective imaging region in the solid-state image pickup device 1 is defined by an opening 5*a* of the X-ray shielding member 5.

The signal output section 20 holds a voltage value according to the amount of charge output from each pixel P, and converts the held voltage value to a digital value to be output to a data bus DB. The signal readout sections 21A to 21H, which are provided corresponding to two or more pixel columns in the pixel array 10A per one signal readout section, hold voltage values according to the charge amounts output from the respective pixels P of the corresponding pixel columns, and output the voltage values to the corresponding A/D converters 22A to 22H, respectively. Similarly, the signal readout sections 21I to 21L, which are provided corresponding to two or more pixel columns in the pixel array 10B per one signal readout section, hold voltage values according to the charge amounts output from the respective pixels P of the corresponding pixel columns, and output the voltage values to the corresponding A/D converters 22I to 22L, respectively. At this time, the scan shift registers 30A and 30B control the respective pixels P so that charges accumulated in the pixels P are sequentially output to the signal readout sections 21A to 21L row by row.

The A/D converters 22A to 22L are input with voltage values output from the corresponding signal readout sections 21A to 21L, and apply A/D conversion processing to the input voltage values (analog values) to generate digital values according to the input voltage values. The A/D converters 22A to 22L output the generated digital values to the FIFO data buffers 23A to 23L corresponding to the A/D converters 22A to 22L.

The FIFO data buffers 23A to 23L, after all digital values corresponding to each of the NA columns contained in the pixel array 10A and the NB columns contained in the pixel array 10B are completed, output the digital values to the data bus DB. At this time, the FIFO data buffers 23A to 23F sequentially output digital values corresponding to each column from the first column to the n-th column ($2 \leq n < NA$) of the pixel array 10A (digital values stored in six FIFO data buffers 23A to 23F arranged on the left side of a boundary line E in FIG. 3) to the data bus DB. In parallel with this output operation, the FIFO data buffers 23G to 23L sequentially output digital values corresponding to each column from the (n+1)-th column of the pixel array 10A through the NA-th column and the first column of the pixel array 10B to the NB-th column (digital values stored in six FIFO data buffers 23G to 23L arranged on the right side of the boundary line E in FIG. 3) to the data bus DB. That is, in terms of a processing unit such as a CPU that controls the data bus DB, the six FIFO data buffers 23A to 23F arranged on the left side of the boundary line E compose one output port, and the six FIFO data buffers 23G to 23L arranged on the right side of the boundary line E compose another output port.

Figure 5:
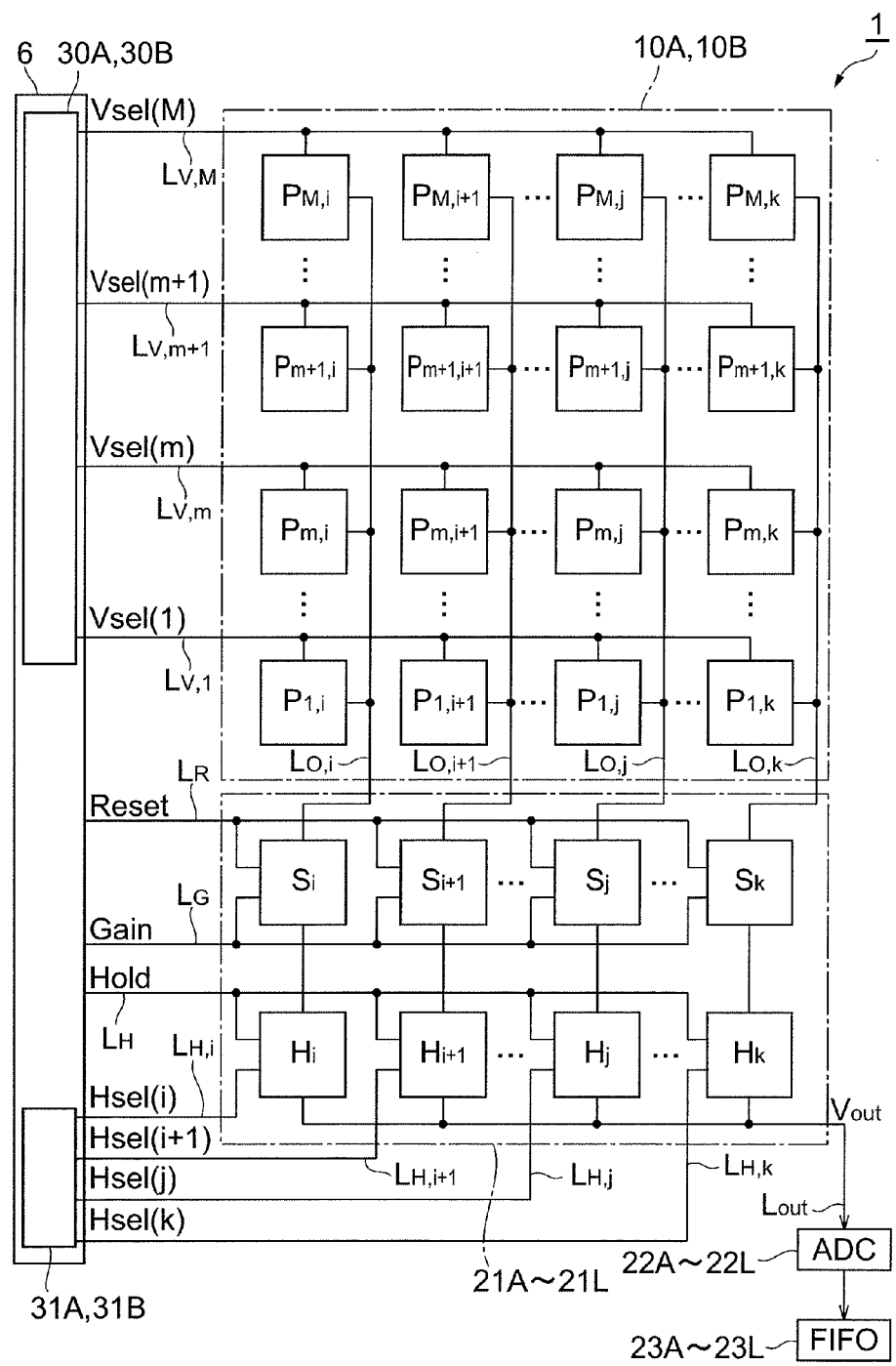
FIG. 5 is a diagram showing an internal configuration of the solid-state image pickup device 1, where a part (pixel block) of a pixel array 10A (10B) corresponding to one of a plurality of signal readout sections 21A to 21L is shown as a representative.

Next, a detailed configuration of the solid-state image pickup device 1 according to the present embodiment will be described. FIG. 5 is a diagram showing an internal configuration of the solid-state image pickup device 1, where a part (pixel block) of the pixel array 10A (10B) corresponding to one of a plurality of signal readout sections 21A to 21L is shown as a representative. The pixel block in the pixel array 10A (10B) consists of pixels $P_{1,i}$ to $P_{M,k}$ arrayed two-dimensionally in M rows and (k−i+1) columns. A pixel $P_{m,j}$ is located on the m-th row and the j-th column. Here, i and k are each an integer not less than 1, and satisfy $1 \leq i < k \leq NA$ (or NB). Moreover, m is an integer not less than 1 and not more than M, and j is an integer not less than i and not more than k. Each of the (k−i+1) pixels $P_{m,i}$ to $P_{m,k}$ of the m-th row is connected with the scan shift register 30A (or 30B) by an m-th row selecting wiring line $L_{V,m}$. Here, in FIG. 5, the scan shift registers 30A and 30B are included in a control section 6. An output terminal of each of the M pixels $P_{1,j}$ to $P_{M,j}$ of the j-th column is connected to an integration circuit $S_j$ of the signal readout sections 21A to 21L by a j-th column readout wiring line $L_{O,j}$.

Each of the signal readout sections 21A to 21L includes (k−i+1) integration circuits $S_i$ to $S_k$ and (k−i+1) holding circuits $H_i$ to $H_k$. The respective integration circuits $S_j$ have a common configuration. Moreover, the respective holding circuits $H_j$ have a common configuration. Each integration circuit $S_j$ has an input terminal connected to the readout wiring line $L_{O,j}$, accumulates charges input to this input terminal, and outputs a voltage value according to the accumulated charge amount from an output terminal to the holding circuit $H_j$. Each of the (k−i+1) integration circuits $S_i$ to $S_k$ is connected with the control section 6 by a reset wiring line $L_R$, and also connected with the control section 6 by a gain setting wiring line $L_G$. Each holding circuit $H_j$ has an input terminal connected to the output terminal of the integration circuit $S_j$, holds the voltage value input to this input terminal, and outputs the held voltage value from an output terminal to a voltage output wiring line $L_{out}$. Each of the (k−i+1) holding circuits $H_i$ to $H_k$ is connected with the control section 6 by a hold wiring line $L_H$. Moreover, each holding circuit $H_j$ is connected with a readout shift register 31A (or 31B) of the control section 6 by a j-th column selecting wiring line $L_{H,j}$.

The A/D converters 22A to 22L are input with a voltage value output to the voltage output wiring line $L_{out}$ from each of the (k−i+1) holding circuits $H_i$ to $H_k$, and applies A/D conversion processing to the input voltage value (analog value) to output a digital value according to the input voltage value to each of the FIFO data buffers 23A to 23L.

The scan shift register 30A (30B) of the control section 6 outputs an m-th row selection controlling signal Vsel(m) to the m-th row selecting wiring line $L_{V,m}$ to supply this m-th row selection controlling signal Vsel(m) to each of the (k−i+1) pixels $P_{m,i}$ to $P_{m,k}$ of the m-th row. M row selection controlling signals Vsel(1) to Vsel(M) sequentially take significant values. Moreover, the readout shift register 31A (31B) of the control section 6 outputs a j-th column selection controlling signal Hsel(j) to the j-th column selecting wiring line $L_{H,j}$ to supply this j-th column selection controlling signal Hsel(j) to the holding circuit $H_j$. (k−i+1) column selection controlling signals Hsel(i) to Hsel(k) also sequentially take significant values.

Moreover, the control section 6 outputs a reset controlling signal Reset to the reset wiring line $L_R$ to supply this reset controlling signal Reset to each of the (k−i+1) integration circuits $S_i$ to $S_k$. The control section 6 outputs a gain setting signal Gain to the gain setting wiring line $L_G$ to supply this gain setting signal Gain to each of the (k−i+1) integration circuits $S_i$ to $S_k$. The control section 6 outputs a hold controlling signal Hold to the hold wiring line $L_H$ to supply this hold controlling signal Hold to each of the (k−i+1) holding circuits $H_i$ to $H_k$. Further, the control section 6 also controls A/D conversion processing in the A/D converters 22A to 22L, which is not shown.

Figure 6:
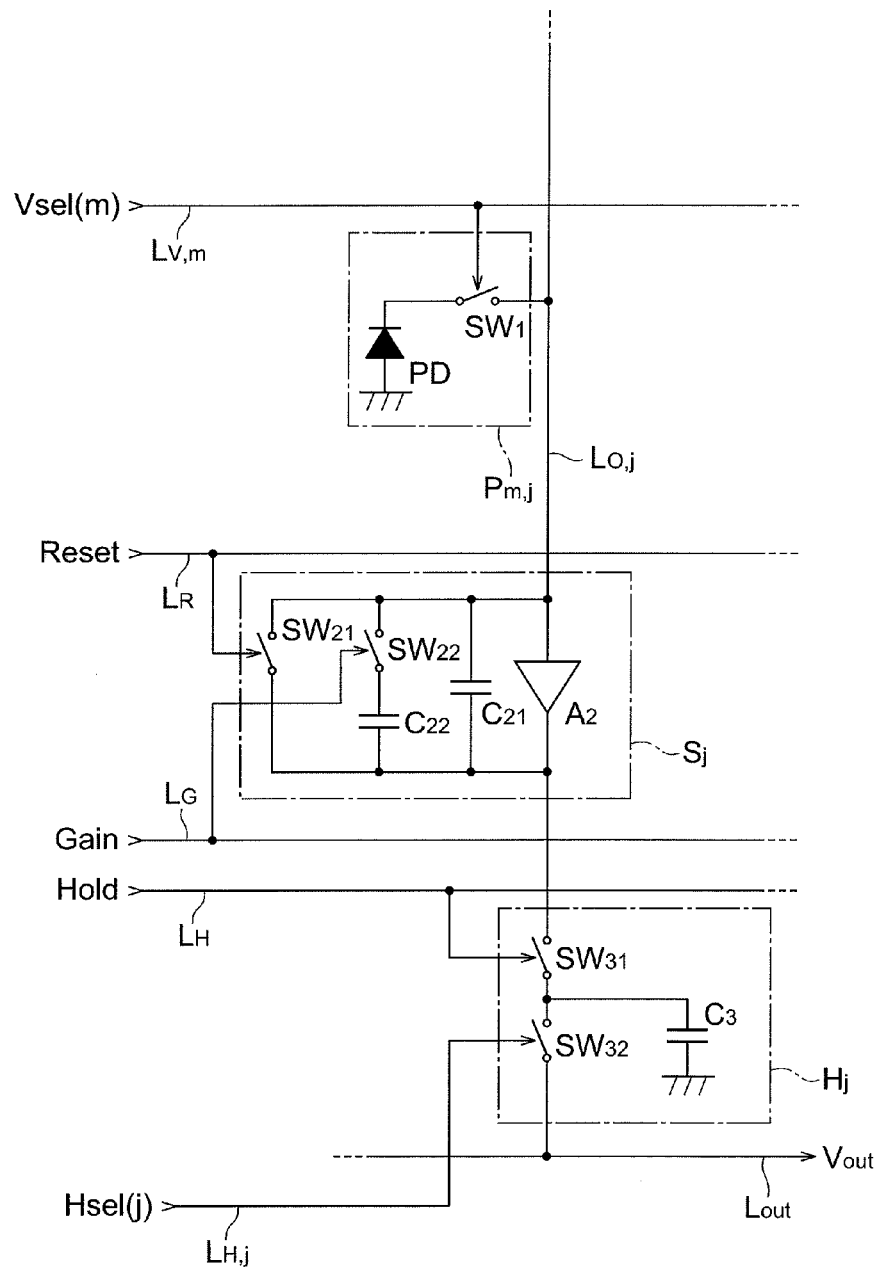
FIG. 6 is a circuit diagram of each of the pixel $P_{m,j}$ included in the pixel block of the solid-state image pickup device 1, the integration circuit $S_j$, and the holding circuit $H_j$.

FIG. 6 is a circuit diagram of each of the pixel $P_{m,j}$ included in the pixel block of the solid-state image pickup device 1, the integration circuit $S_j$, and the holding circuit $H_j$. Here, a circuit diagram of the pixel $P_{m,j}$ as a representative of the pixels $P_{1,i}$ to $P_{M,k}$ is shown, a circuit diagram of the integration circuit $S_j$ as a representative of the (k−i+1) integration circuits $S_i$ to $S_k$ is shown, and a circuit diagram of the holding circuit $H_j$ as a representative of the (k−i+1) holding circuits $H_i$ to $H_k$ is shown. That is, a circuit portion relating to the pixel $P_{m,j}$ on the m-th row and the j-th column and the j-th column readout wiring line $L_{O,j}$ is shown.

The pixel $P_{m,j}$ includes a photodiode PD and a readout switch $SW_1$. The anode terminal of the photodiode PD is grounded, and the cathode terminal of the photodiode PD is connected to the j-th column readout wiring line $L_{O,j}$ via the readout switch $SW_1$. The photodiode PD generates charge of an amount according to an incident light intensity, and accumulates the generated charge in a junction capacitance section. The readout switch $SW_1$ is supplied with the m-th row selection controlling signal Vsel(m) passed through the m-th row selecting wiring line $L_{V,m}$ from the control section 6. The m-th row selection controlling signal Vsel(m) is a signal that instructs an opening and closing operation of the readout switch $SW_1$ in each of the NA pixels $P_{m,1}$ to $P_{m,NA}$ of the m-th row in the pixel array 10A and the NB pixels $P_{m,1}$ to $P_{m,NB}$ of the m-th row in the pixel array 10B.

In this pixel $P_{m,j}$, when the m-th row selection controlling signal Vsel(m) is at low level, the readout switch $SW_1$ opens, and a charge generated in the photodiode PD is not output to the j-th column readout wiring line $L_{O,j}$ but is accumulated in the junction capacitance section. On the other hand, when the m-th row selection controlling signal Vsel(m) is at high level, the readout switch $SW_1$ closes, and the charge generated in the photodiode PD and accumulated in the junction capacitance section until then is output to the j-th column readout wiring line $L_{O,j}$ through the readout switch $SW_1$.

The j-th column readout wiring line $L_{O,j}$ is connected to the readout switch $SW_1$ in each of the M pixels $P_{1,j}$ to $P_{M,j}$ of the j-th column in the pixel array 10A (or 10B). The j-th column readout wiring line $L_{O,j}$ reads out a charge generated in the photodiode PD of any of the M pixels $P_{1,j}$ to $P_{M,j}$ via the readout switch $SW_1$ of this pixel, and transfers the charge to the integration circuit $S_j$.

The integration circuit $S_j$ includes an amplifier $A_2$, an integrating capacitive element $C_{21}$, an integrating capacitive element $C_{22}$, a discharge switch $SW_{21}$, and a gain setting switch $SW_{22}$. The integrating capacitive element $C_{21}$ and the discharge switch $SW_{21}$ are connected in parallel to each other, and provided between an input terminal and an output terminal of the amplifier $A_2$. Moreover, the integrating capacitive element $C_{22}$ and the gain setting switch $SW_{22}$ are connected in series to each other, and provided between the input terminal and the output terminal of the amplifier $A_2$ so that the gain setting switch $SW_{22}$ is connected to the input terminal side of the amplifier $A_2$. The input terminal of the amplifier $A_2$ is connected to the j-th column readout wiring line $L_{O,j}$.

The discharge switch $SW_{21}$ is supplied with the reset controlling signal Reset through the reset wiring line $L_R$ from the control section 6. The reset controlling signal Reset is a signal that instructs an opening and closing operation of the discharge switch $SW_{21}$ in each of the NA integration circuits $S_1$ to $S_{NA}$ corresponding to the pixel array 10A and the NB integration circuits $S_1$ to $S_{NB}$ corresponding to the pixel array 10B. The gain setting switch $SW_{22}$ is supplied with the gain setting signal Gain through the gain setting wiring line $L_G$ from the control section 6. The gain setting signal Gain is a signal that instructs an opening and closing operation of the gain setting switch $SW_{22}$ in each of the NA integration circuits $S_1$ to $S_{NA}$ corresponding to the pixel array 10A and the NB integration circuits $S_1$ to $S_{NB}$ corresponding to the pixel array 10B.

In this integration circuit $S_j$, the integrating capacitive elements $C_{21}$, $C_{22}$ and the gain setting switch $SW_{22}$ compose a feedback capacitance section where the capacitance value is variable. That is, when the gain setting signal Gain is at low level and the gain setting switch $SW_{22}$ is open, the capacitance value of the feedback capacitance section is equal to a capacitance value of the integrating capacitive element $C_{21}$.

On the other hand, when the gain setting signal Gain is at high level and the gain setting switch $SW_{22}$ is closed, the capacitance value of the feedback capacitance section is equal to a sum of respective capacitance values of the integrating capacitive elements $C_{21}$, $C_{22}$. When the reset controlling signal Reset is at high level, the discharge switch $SW_{21}$ closes, the feedback capacitance section is discharged, and a voltage value to be output from the integration circuit $S_j$ is initialized. On the other hand, when the reset controlling signal Reset is at low level, the discharge switch $SW_{21}$ opens, a charge input to the input terminal is accumulated in the feedback capacitance section, and a voltage value according to the accumulated charge amount is output from the integration circuit $S_j$.

The holding circuit $H_j$ includes an input switch $SW_{31}$, an output switch $SW_{32}$, and a holding capacitive element $C_3$. One end of the holding capacitive element $C_3$ is grounded. The other end of the holding capacitive element $C_3$ is connected to the output terminal of the integration circuit $S_j$ via the input switch $SW_{31}$, and connected to the voltage output wiring line $L_{out}$ via the output switch $SW_{32}$. The input switch $SW_{31}$ is supplied with the hold controlling signal Hold passed through the hold wiring line $L_H$ from the control section 6. The hold controlling signal Hold is a signal that instructs an opening and closing operation of the input switch $SW_{31}$ in each of the NA holding circuits $H_1$ to $H_{NA}$ corresponding to the pixel array 10A and the NB holding circuits $H_1$ to $H_{NB}$ corresponding to the pixel array 10B. The output switch $SW_{32}$ is supplied with the j-th column selection controlling signal Hsel(j) passed through the j-th column selecting wiring line $L_{H,j}$ from the control section 6. The j-th column selection controlling signal Hsel(j) is a signal that instructs an opening and closing operation of the output switch $SW_{32}$ of the holding circuit $H_j$.

In this holding circuit $H_j$, when the hold controlling signal Hold switches from high level to low level, the input switch $SW_{31}$ switches from a closed state to an open state, and a voltage value being input to the input terminal at this time is held in the holding capacitive element $C_3$. Moreover, when the j-th column selection controlling signal Hsel(j) is at high level, the output switch $SW_{32}$ closes, and the voltage value held in the holding capacitive element $C_3$ is output to the voltage output wiring line $L_{out}$.

The control section 6, when outputting a voltage value according to a received light intensity in each of the (k−i+1) pixels $P_{m,i}$ to $P_{m,k}$ of the m-th row in the pixel array 10A (or 10B), instructs temporary closing and then opening of the discharge switch $SW_{21}$ in each of the (k−i+1) integration circuits $S_i$ to $S_k$ by the reset controlling signal Reset, and then instructs closing of the readout switch $SW_1$ in each of the (k−i+1) pixels $P_{m,i}$ to $P_{m,k}$ of the m-th row in the pixel array 10A (10B) for a predetermined period by the m-th row selection controlling signal Vsel(m). The control section 6, in this predetermined period, instructs switching of the input switch $SW_{31}$ in each of the (k−i+1) holding circuits $H_i$ to $H_k$ from a closed state to an open state by the hold controlling signal Hold. Then, the control section 6, after the predetermined period, instructs sequential closing of the output switches $SW_{32}$ in the respective (k−i+1) holding circuits $H_i$ to $H_k$ for a certain period by the column selection controlling signals Hsel(i) to Hsel(k). The control section 6 performs such control as in the above for the respective rows in sequence.

Thus, the control section 6 controls an opening and closing operation of the readout switch $SW_1$ in each of the pixels $P_{1,j}$ to $P_{M,k}$ contained in each pixel block of the pixel array 10A (10B), and controls a holding operation and an output operation of the voltage values in the signal readout sections 21A to 21L. Accordingly, the control section 6 makes a voltage value according to the amount of charge generated in the photodiode PD of each of the M×(k−i+1) pixels $P_{1,i}$ to $P_{M,k}$ be repeatedly output frame by frame from the signal readout sections 21A to 21L.

Next, operation of the solid-state image pickup device 1 will be described in detail. In the solid-state image pickup device 1, as a result of level changes of each of the M row selection controlling signals Vsel(1) to Vsel(M), the (NA+NB) column selection controlling signals Hsel(1) to Hsel(NA) and Hsel(1) to Hsel(NB), the reset controlling signal Reset, and the hold controlling signal Hold at predetermined timings under control by the control section 6, an optical image made incident on the pixel arrays 10A and 10B can be imaged to obtain frame data. Here, in the following description, the gain setting switch $SW_{22}$ is supposed to be closed.

Figure 7:
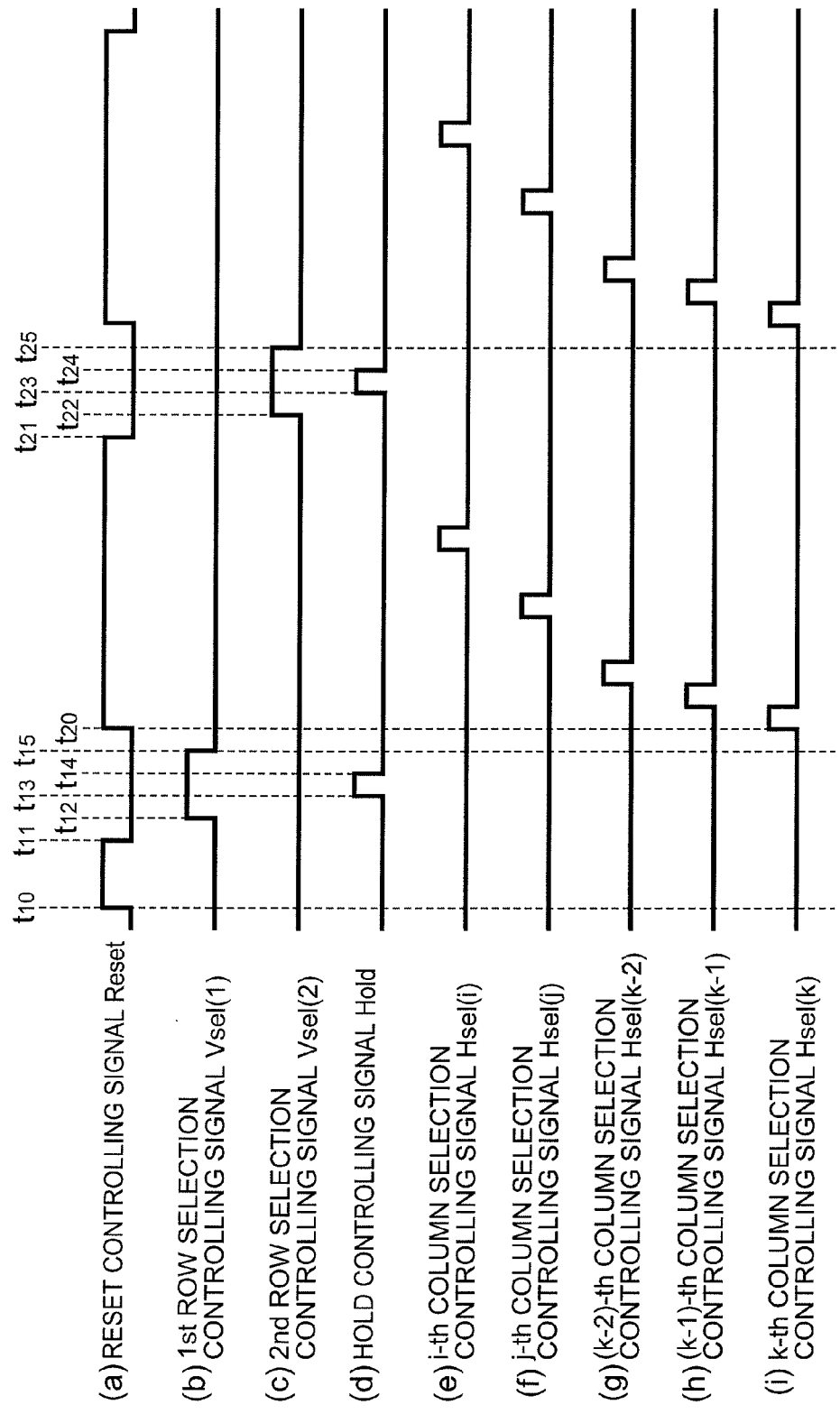
FIG. 7 is a timing chart for explaining operation of a pixel block included in the first column to the n-th column of the pixel array 10A, and operation of a signal output section 20 corresponding to this pixel block.

FIG. 7 is a timing chart for explaining operation of a pixel block included in the first column to the n-th column of the pixel array 10A (pixel array on the left side of the boundary line E shown in FIG. 3), and operation of the signal output section 20 corresponding to this pixel block. This figure shows, in order from the top, (a) the reset controlling signal Reset for instructing an opening and closing operation of the discharge switch $SW_{21}$ in each of the integration circuits $S_i$ to $S_k$, (b) the first row selection controlling signal Vsel(1) for instructing an opening and closing operation of the readout switch $SW_1$ in each of the pixels $P_{1,i}$ to $P_{1,k}$ of the first row in the pixel block, (c) the second row selection controlling signal Vsel(2) for instructing an opening and closing operation of the readout switch $SW_1$ in each of the pixels $P_{2,i}$ to $P_{2,k}$ of the second row in the pixel block, and (d) the hold controlling signal Hold for instructing an opening and closing operation of the input switch $SW_{31}$ in each of the holding circuits $H_i$ to $H_k$.

Moreover, this figure further goes on to show, in order, (e) the i-th column selection controlling signal Hsel(i) for instructing an opening and closing operation of the output switch $SW_{32}$ of the holding circuit $H_i$, (f) the j-th column selection controlling signal Hsel(j) for instructing an opening and closing operation of the output switch $SW_{32}$ of the holding circuit $H_j$, (g) the (k−2)-th column selection controlling signal Hsel(k−2) for instructing an opening and closing operation of the output switch $SW_{32}$ of the holding circuit $H_{k-2}$, (h) the (k−1)-th column selection controlling signal Hsel(k−1) for instructing an opening and closing operation of the output switch $SW_{32}$ of the holding circuit $H_{k-1}$/and (i) the k-th column selection controlling signal Hsel(k) for instructing an opening and closing operation of the output switch $SW_{32}$ of the holding circuit $H_k$.

A charge generated in the photodiode PD of each of the (k−i+1) pixels $P_{1,i}$ to $P_{1,k}$ of the first row and accumulated in the junction capacitance section is read out as follows. Before the time $t_{10}$, each of the M row selection controlling signals Vsel(1) to Vsel(M), the (k−i+1) column selection controlling signals Hsel(i) to Hsel(k), the reset controlling signal Reset, and the hold controlling signal Hold is at low level.

During a period from the time $t_{10}$ to the time $t_{11}$, the reset controlling signal Reset to be output from the control section 6 to the reset wiring line $L_R$ becomes high level, and accordingly, in each of the (k−i+1) integration circuits $S_i$ to $S_k$, the discharge switch $SW_{21}$ closes, and the integrating capacitive elements $C_{21}$, $C_{22}$ are discharged. Moreover, during a period from the time $t_{12}$ to the time $t_{15}$ after the time $t_{11}$, the first row selection controlling signal Vsel(1) to be output from the control section 6 to the first row selecting wiring line $L_{V,1}$ becomes high level, and accordingly, the readout switch $SW_1$ in each of the (k−i+1) pixels $P_{1,i}$ to $P_{1,k}$ of the first row in the pixel block closes.

In the period ($t_{12}$ to $t_{15}$), during a period from the time $t_{13}$ to the time $t_{14}$, the hold controlling signal Hold to be output from the control section 6 to the hold wiring line $L_H$ becomes high level, and accordingly, the input switch $SW_{31}$ in each of the (k−i+1) holding circuits $H_i$ to $H_k$ closes.

In the period ($t_{12}$ to $t_{15}$), the readout switch $SW_1$ in each pixel $P_{1,j}$ of the first row is closed, and the discharge switch $SW_{21}$ of each integration circuit $S_j$ is opened. Therefore, a charge generated in the photodiode PD of the pixel $P_{1,j}$ and accumulated in the junction capacitance section until then is transferred to and accumulated in the integrating capacitive elements $C_{21}$, $C_{22}$ of the integration circuit $S_j$ through the readout switch $SW_1$ of the pixel $P_{1,j}$ and the j-th column readout wiring line $L_{O,j}$. Then, a voltage value corresponding to the amount of charge accumulated in the integrating capacitive elements $C_{21}$, $C_{22}$ of each integration circuit $S_j$ is output from the output terminal of the integration circuit $S_j$.

At the time $t_{14}$ in the period ($t_{12}$ to $t_{15}$), as a result of the hold controlling signal Hold switching from high level to low level, in each of the (k−i+1) holding circuits $H_i$ to $H_k$, the input switch $SW_{31}$ switches from a closed state to an open state, and the voltage value being output from the output terminal of the integration circuit $S_j$ and being input to the input terminal of the holding circuit $H_j$ at this time is held in the holding capacitive element $C_3$.

Then, after the period ($t_{12}$ to $t_{15}$), the column selection controlling signals Hsel(i) to Hsel(k) to be output from the control section 6 to the column selecting wiring lines $L_{H,i}$ to $L_{H,k}$ become high level for a predetermined period in reverse order starting from Hsel(k) (that is, in descending order of the column numbers), and accordingly, the output switches $SW_{32}$ in the respective (k−i+1) holding circuits $H_i$ to $H_k$ close for the predetermined period in, reverse order, the voltage values held in the holding capacitive elements $C_3$ of the respective holding circuits $H_j$ are output in reverse order to the voltage output wiring line $L_{out}$ through the output switches $SW_{32}$. The voltage value $V_{out}$ to be output to the voltage output wiring line $L_{out}$ indicates the received light intensity in the photodiode PD of each of the (k−i+1) pixels $P_{1,i}$ to $P_{1,k}$ of the first row. The voltage values output in reverse order from the respective (k−i+1) holding circuits $H_i$ to $H_k$ are input to any of the A/D converters 22A to 22L, and converted to digital values according to the input voltage values.

Subsequently, a charge generated in the photodiode PD of each of the (k−i+1) pixels $P_{2,i}$ to $P_{2,k}$ of the second row and accumulated in the junction capacitance section is read out as follows.

During a period from the time $t_{20}$ where the column selection controlling signal Hsel(k) becomes high level in the above-described operation to the time $t_{21}$ after where the column selection controlling signal Hsel(i) once becomes high level and then becomes low level, the reset controlling signal Reset to be output from the control section 6 to the reset wiring line $L_R$ becomes high level, and accordingly, in each of the (k−i+1) integration circuits $S_i$ to $S_k$, the discharge switch $SW_{21}$ closes, and the integrating capacitive elements $C_{21}$, $C_{22}$ are discharged. Moreover, during a period from the time $t_{22}$ to the time $t_{25}$ after the time $t_{21}$, the second row selection controlling signal Vsel(2) to be output from the control section 6 to the second row selecting wiring line $L_{V,2}$ becomes high level, and accordingly, the readout switch $SW_1$ in each of the (k−i+1) pixels $P_{2,i}$ to $P_{2,k}$ of the second row in the pixel block closes.

In the period ($t_{22}$ to $t_{25}$), during a period from the time $t_{23}$ to the time $t_{24}$, the hold controlling signal Hold to be output from the control section 6 to the hold wiring line $L_H$ becomes high level, and accordingly, the input switch $SW_{31}$ in each of the (k−i+1) holding circuits $H_i$ to $H_k$ closes.

Then, after the period ($t_{22}$ to $t_{25}$), the column selection controlling signals Hsel(i) to Hsel(k) to be output from the control section 6 to the column selecting wiring lines $L_{H,i}$ to $L_{H,k}$ become high level for a predetermined period in reverse order starting from Hsel(k), and accordingly, the output switches $SW_{32}$ in the respective (k−i+1) holding circuits $H_i$ to $H_k$ close for the predetermined period in reverse order. Thus, a voltage value $V_{out}$ indicating the received light intensity in the photodiode PD of each of the (k−i+1) pixels $P_{2,i}$ to $P_{2,k}$ of the second row is output to the voltage output wiring line $L_{out}$. The voltage values output in reverse order from the respective (k−i+1) holding circuits $H_i$ to $H_k$ are input to any of the A/D converters 22A to 22L, and converted to digital values according to the input voltage values.

Figure 8:
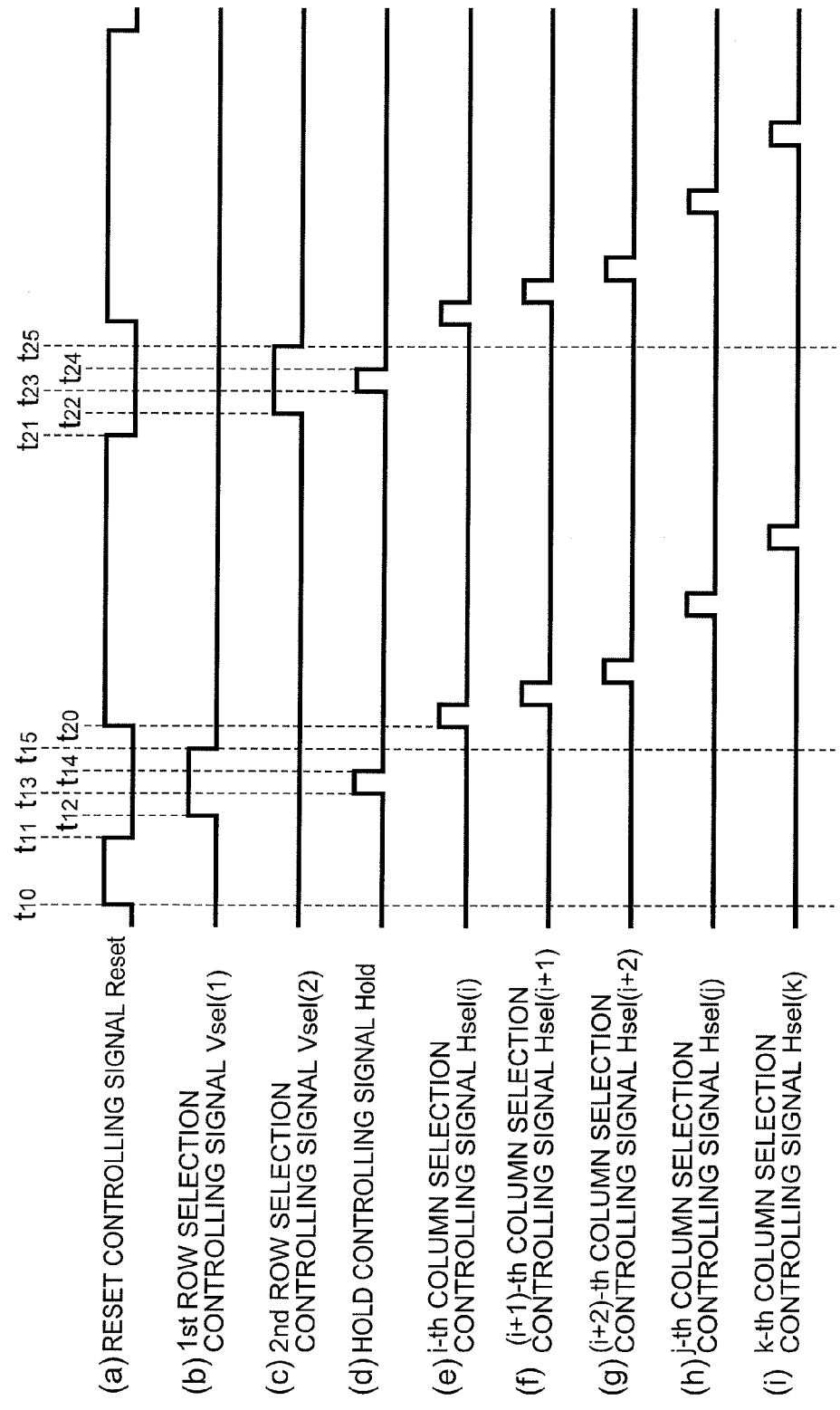
FIG. 8 is a timing chart for explaining operation of a pixel block included in the (n+1)-th column to the NA-th column of the pixel array 10A and the first column to the NB-th column of the pixel array 10B, and operation of the signal output section 20 corresponding to this pixel block.

FIG. 8 is a timing chart for explaining operation of a pixel block included in the (n+1)-th column to the NA-th column of the pixel array 10A and the first column to the NB-th column of the pixel array 10B (pixel array on the right side of the boundary line E shown in FIG. 3), and operation of the signal output section 20 corresponding to this pixel block. This figure shows, in order from the top, (a) the reset controlling signal Reset, (b) the first row selection controlling signal Vsel(1), (c) the second row selection controlling signal Vsel(2), and (d) the hold controlling signal Hold. Here, the operation of these signals is the same as that shown in (a) to (d) in FIG. 7, and the operation of the pixels $P_{1,i}$ to $P_{M,k}$, the integration circuits $S_i$ to $S_k$, and the holding circuits $H_i$ to $H_k$ is also the same as the above-described operation except for the output order of the holding circuits $H_i$ to $H_k$, and thus a detailed description of these will be omitted.

Moreover, this figure further goes on to show, in order, (e) the i-th column selection controlling signal Hsel(i) for instructing an opening and closing operation of the output switch $SW_{32}$ of the holding circuit $H_i$, (f) the (i+1)-th column selection controlling signal Hsel(i+1) for instructing an opening and closing operation of the output switch $SW_{32}$ of the holding circuit $H_{i+1}$, (g) the (i+2)-th column selection controlling signal Hsel(i+2) for instructing an opening and closing operation of the output switch $SW_{32}$ of the holding circuit $H_{i+2}$, (h) the j-th column selection controlling signal Hsel(j) for instructing an opening and closing operation of the output switch $SW_{32}$ of the holding circuit $H_j$, and (i) the k-th column selection controlling signal Hsel(k) for instructing an opening and closing operation of the output switch $SW_{32}$ of the holding circuit $H_k$.

After the period ($t_{10}$ to $t_{15}$) where a charge generated in the photodiode PD of each of the (k−i+1) pixels $P_{1,i}$ to $P_{1,k}$ of the first row and accumulated in the junction capacitance section is read out, and held in the holding capacitive element $C_3$ of each holding circuit $H_j$, the column selection controlling signals Hsel(i) to Hsel(k) to be output from the control section 6 to the column selecting wiring lines $L_{H,i}$ to $L_{H,k}$ become high level for a predetermined period in forward order starting from Hsel(i) (that is, in ascending order of the column numbers), and accordingly, the output switches $SW_{32}$ in the respective (k−i+1) holding circuits $H_i$ to $H_k$ close for the predetermined period in forward order, and the voltage values held in the holding capacitive elements $C_3$ of the respective holding circuits $H_j$ are output in forward order to the voltage output wiring line $L_{out}$ through the output switches $SW_{32}$. The voltage values output in forward order from the respective (k−i+1) holding circuits $H_i$ to $H_k$ are input to any of the A/D converters 22A to 22L, and converted to digital values according to the input voltage values.

Subsequently, after the period ($t_{21}$ to $t_{25}$) where a charge generated in the photodiode PD of each of the (k−i+1) pixels $P_{2,i}$ to $P_{2,k}$ of the second row is read out, and held in the holding capacitive element $C_3$ of each holding circuit $H_j$, the column selection controlling signals Hsel(i) to Hsel(k) to be output from the control section 6 to the column selecting wiring lines $L_{H,i}$ to $L_{H,k}$ become high level for a predetermined period in forward order starting from Hsel(i), and accordingly, the output switches $SW_{32}$ in the respective (k−i+1) holding circuits $H_i$ to $H_k$ close for the predetermined period in forward order. Thus, a voltage value $V_{out}$ indicating the received light intensity in the photodiode PD of each of the (k−i+1) pixels $P_{2,i}$ to $P_{2,k}$ of the second row is output to the voltage output wiring line $L_{out}$. The voltage values output in forward order from the respective (k−i+1) holding circuits $H_i$ to $H_k$ are input to any of the A/D converters 22A to 22L, and converted to digital values according to the input voltage values.

Subsequent to the operation for the first row and the second row shown in FIG. 7 and FIG. 8, the same operation is performed for the third row to the M-th row, so that frame data indicating an image captured in one time of imaging is obtained. Further, when the operation ends with respect to the M-th row, the same operation is again performed in a range from the first row to the M-th row, and frame data indicating a next image is obtained. By thus repeating the same operation with a predetermined period, voltage values $V_{out}$ indicating a two-dimensional intensity distribution of an optical image received by the pixel block are output to the voltage output wiring line $L_{out}$, and the frame data is repeatedly obtained.

Figure 9:
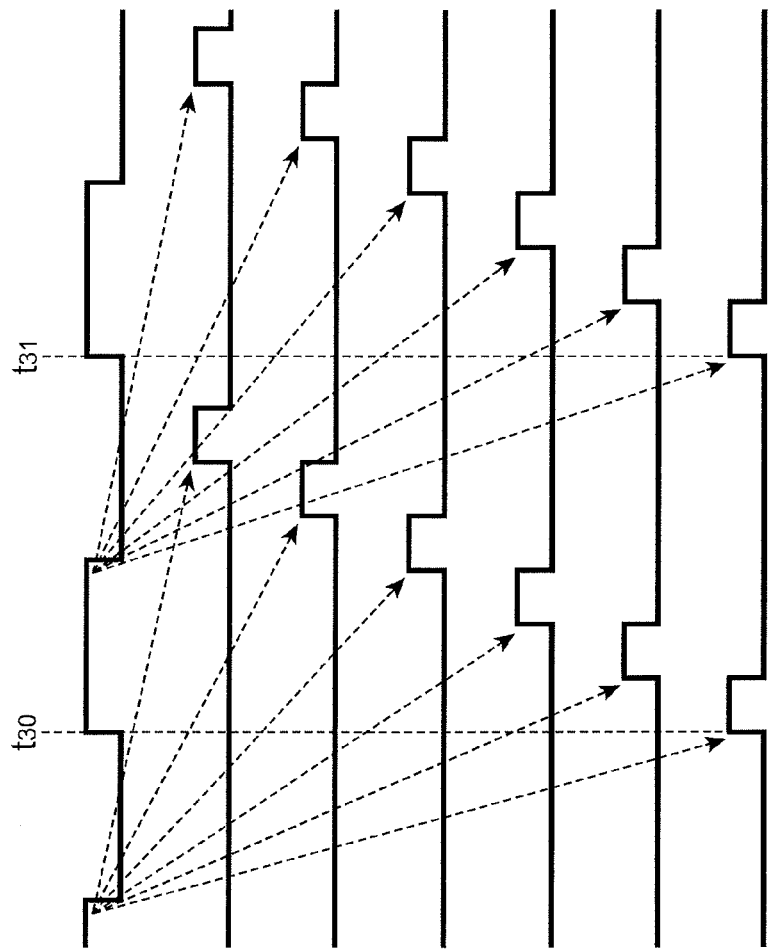
FIG. 9 is a timing chart for explaining an input/output operation of FIFO data buffers 23A to 23F provided corresponding to the pixel block included in the first column to the n-th column of the pixel array 10A.

Subsequently, operation of the FIFO data buffers 23A to 23L will be described. FIG. 9 is a timing chart for explaining an input/output operation of the FIFO data buffers 23A to 23F provided corresponding to pixel blocks included in the first column to the n-th column of the pixel array 10A (pixel array on the left side of the boundary line E shown in FIG. 3). This figure shows, in order from the top, (a) the timing where the digital values are written to the FIFO data buffers 23A to 23F from the A/D converters 22A to 22F, (b) the timing where the digital value stored in the FIFO data buffer 23A is read out, (c) the timing where the digital value stored in the FIFO data buffer 23B is read out, (d) the timing where the digital value stored in the FIFO data buffer 23C is read out, (e) the timing where the digital value stored in the FIFO data buffer 23D is read out, (f) the timing where the digital value stored in the FIFO data buffer 23E is read out, and (g) the timing where the digital value stored in the FIFO data buffer 23F is read out.

As shown in FIG. 9(a), the writing operation of digital values from the A/D converters 22A to 22F into the FIFO data buffers 23A to 23F is performed simultaneously and in parallel in the respective FIFO data buffers 23A to 23F. Then, at almost the same timing as the timing (time $t_{30}$ in the figure) where an operation to write digital values corresponding to, of the first row to the M-th row that compose the pixel arrays 10A, 10B, the m-th row into the FIFO data buffers 23A to 23F is started, digital values corresponding to the previous (m−1)-th row begin to be read out from the FIFO data buffers 23A to 23F via the data bus DB (refer to FIG. 3).

At this time, the digital values stored in the FIFO data buffers 23A to 23F are read out, starting from the FIFO data buffer 23F up until the FIFO data buffer 23A, in a reverse order to the column numbers in the pixel arrays 10A, 10B. Specifically, the readout operation from the FIFO data buffer 23E is started (FIG. 9(f)) after the readout operation from the FIFO data buffer 23F (FIG. 9(g)) ends, the readout operation from the FIFO data buffer 23D is started (FIG. 9(e)) after the readout operation from the FIFO data buffer 23E ends, and subsequently, the digital values are read out in this order from the respective FIFO data buffers until the readout from the FIFO data buffer 23A ends (FIG. 9(b)).

As in the above, the column-by-column voltage values held in the respective signal readout sections 21A to 21F are output to the corresponding A/D converters 22A to 22F in a reverse order with respect to the column numbers. Then, the digital values output from the A/D converters 22A to 22F are written simultaneously and in parallel into the FIFO data buffers 23A to 23F, and the digital values are read out in this order (that is, in a reverse order to the column numbers) also when being read out via the data bus DB. Therefore, by starting readout from the FIFO data buffer 23F as mentioned above, the signal output section 20 outputs digital values corresponding to the respective columns from the first column to the n-th column of the pixel array 10A, sequentially starting from the n-th column up until the first column, in a reverse order to the column numbers.

The FIFO data buffers 23A to 23F output digital values corresponding to the (m−1)-th row to the data bus DB in this manner, and then output, to the data bus DB, digital values corresponding to the m-th row input in parallel with the outputting operation of the digital values, at almost the same timing as the time $t_{31}$ in the figure (timing where an operation to write digital values corresponding to the m+1-th row into the FIFO data buffers 23A to 23F is started) and in the same order when having output digital values corresponding to the (m−1)-th row. As a result of such operation being performed for the first row to the M-th row, frame data is output to the data bus DB. Moreover, when the operation ends with respect to the M-th row, the same operation is again performed in a range from the first row to the M-th row, and frame data indicating a next image is output.

Figure 10:
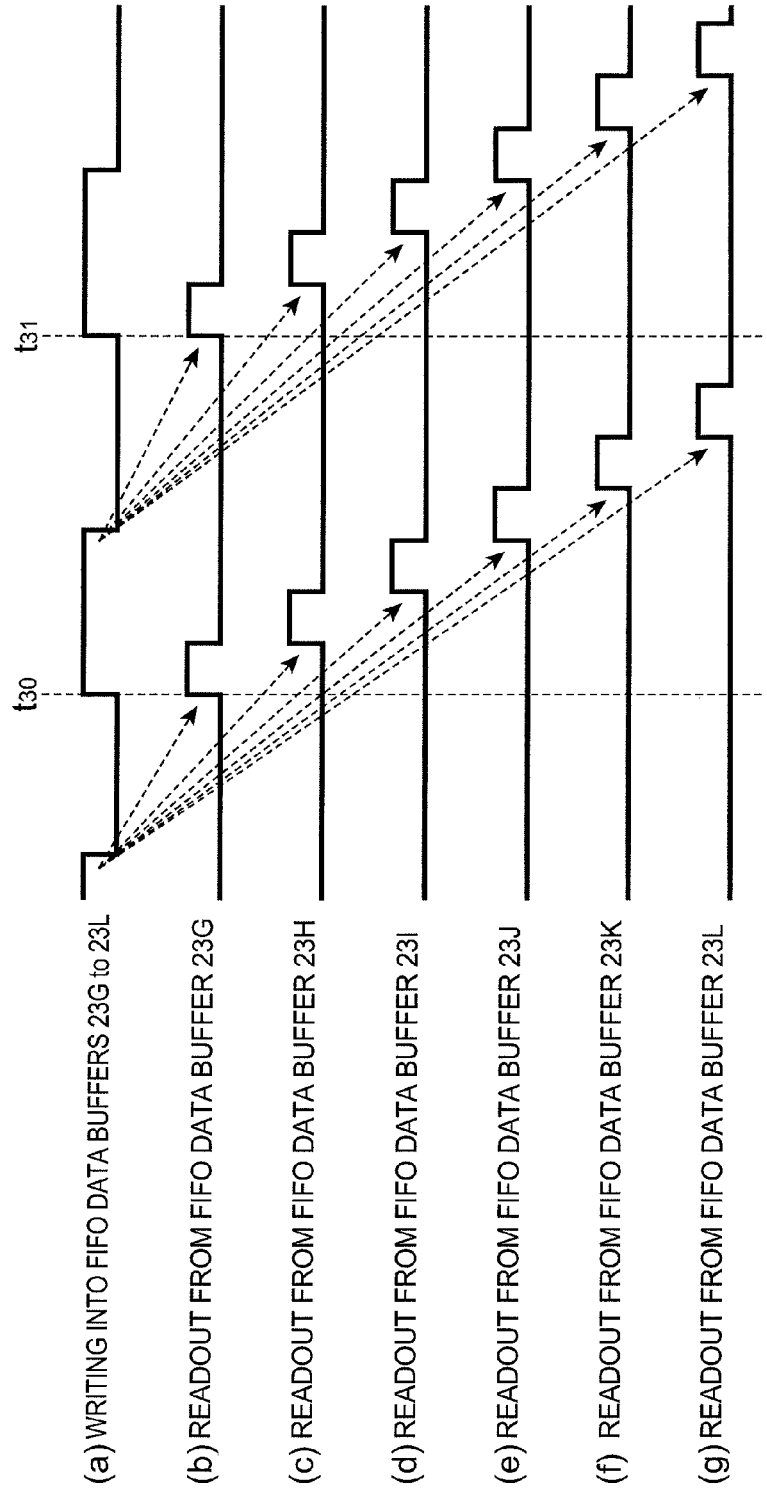
FIG. 10 is a timing chart for explaining an input/output operation of FIFO data buffers 23G to 23L provided corresponding to the pixel block included in the (n+1)-th column to the NA-th column of the pixel array 10A and the first column to the NB-th column of the pixel array 10B.

FIG. 10 is a timing chart for explaining an input/output operation of the FIFO data buffers 23G to 23L provided corresponding to pixel blocks included in the (n+1)-th column to the NA-th column of the pixel array 10A and the first column to the NB-th column of the pixel array 10B (pixel array on the right side of the boundary line E shown in FIG. 3). This figure shows, in order from the top, (a) the timing where the digital values are written to the FIFO data buffers 23G to 23L from the A/D converters 22G to 22L, (b) the timing where the digital value stored in the FIFO data buffer 23G is read out, (c) the timing where the digital value stored in the FIFO data buffer 23H is read out, (d) the timing where the digital value stored in the FIFO data buffer 23I is read out, (e) the timing where the digital value stored in the FIFO data buffer 23J is read out, (f) the timing where the digital value stored in the FIFO data buffer 23K is read out, and (g) the timing where the digital value stored in the FIFO data buffer 23L is read out.

As shown in FIG. 10(a), the writing operation of digital values from the A/D converters 22G to 22L into the FIFO data buffers 23G to 23L is performed simultaneously and in parallel in the respective FIFO data buffers 23G to 23L. Then, at almost the same timing as the timing (time $t_{30}$ in the figure) where an operation to write digital values corresponding to, of the first row to the M-th row that compose the pixel arrays 10A, 10B, the m-th row into the FIFO data buffers 23G to 23L is started, digital values corresponding to the previous (m−1)-th row begin to be read out from the FIFO data buffers 23G to 23L via the data bus DB (refer to FIG. 3).

At this time, the digital values stored in the FIFO data buffers 23G to 23L are read out, starting from the FIFO data buffer 23G up until the FIFO data buffer 23L, in a forward order to the column numbers in the pixel arrays 10A, 10B. Specifically, the readout operation from the FIFO data buffer 23H is started (FIG. 10(c)) after the readout operation from the FIFO data buffer 23G (FIG. 10(b)) ends, the readout operation from the FIFO data buffer 23I is started (FIG. 10(d)) after the readout operation from the FIFO data buffer 23H ends, and subsequently, the digital values are read out in this order from the respective FIFO data buffers until the readout from the FIFO data buffer 23L ends (FIG. 10(g)).

As in the above, the column-by-column voltage values held in the respective signal readout sections 21G to 21L are output to the corresponding A/D converters 22G to 22L in a forward order with respect to the column numbers. Then, the digital values output from the A/D converters 22G to 22L are written simultaneously and in parallel into the FIFO data buffers 23G to 23L, and the digital values are read out in this order (that is, in a forward order with respect to the column numbers) also when being read out via the data bus DB. Therefore, by starting readout from the FIFO data buffer 23G as mentioned above, the signal output section 20 outputs digital values corresponding to the respective columns from the (n+1)-th column of the pixel array 10A through the NA-th column and the first column of the pixel array 10B to the NB-th column, sequentially in forward order, that is, in a reverse order to the output order of digital values corresponding to the respective columns from the first column to the n-th column of the pixel array 10A.

The FIFO data buffers 23G to 23L output digital values corresponding to the (m−1)-th row to the data bus DB in this manner, and then output, to the data bus DB, digital values corresponding to the m-th row input in parallel with the outputting operation of the digital values, at almost the same timing as the time $t_{31}$ in the figure (timing where an operation to write digital values corresponding to the m+1-th row into the FIFO data buffers 23G to 23L is started) and in the same order when having output digital values corresponding to the (m−1)-th row. As a result of such operation being performed for the first row to the M-th row, frame data is output to the data bus DB. Moreover, when the operation ends with respect to the M-th row, the same operation is again performed in a range from the first row to the M-th row, and frame data indicating a next image is output.

Effects to be obtained by the solid-state image pickup device 1 of the present embodiment described in the above will be described, along with the problems of the conventional solid-state image pickup device. Generally, the size required for the pixel array of the solid-state image pickup device varies depending on its imaging application, but in, for example, cephalography for dental diagnosis, it is required that the pixel array of the solid-state image pickup device has a long length of 22 cm or more. This is because it is necessary in cephalography, where the positional relationship of a patient's skull and maxillomandibular bones is grasped to obtain information as to at which position a tooth extraction is performed, whether orthodontic treatment for the patient will be simple or difficult, or the like, that the width in the vertical direction of the pixel array covers almost the whole of an adult's head in order to obtain such information.

However, when such a long pixel array is required, it may be difficult, depending on the diameter of a semiconductor wafer to be used for production of the solid-state image pickup device, to prepare the pixel array on a single substrate. In such a case, the required size can be satisfied by arranging two substrates shorter than the size required for a pixel array side by side in the long-length direction, and aligning their respective pixel arrays with each other to be used as one solid-state image pickup device (so-called tiling).

However, when two substrates arranged side by side are used, a dead area C is produced at a boundary part (seam) between the pixel arrays as shown in FIG. 3. Further, depending on the imaging application, such a dead area C may be limited in position. In the case of X-ray photography for dental diagnosis, where two pixel arrays 110A, 110B are tiled in the up-and-down direction to move horizontally in parallel while imaging is performed as shown in (a) in FIG. 11, if the pixel arrays 110A, 110B are equal in width in the vertical direction to each other, the boundary part between the pixel array 110A and the pixel array 110B passes by the ear of the subject A as shown in the same figure. Here, the regions FA and FB shown in the figure indicate imaging ranges by the pixel arrays 110A and 110B, respectively. In cephalography, information concerning the region G from the subject A's jaw to an area including the ear, shown in FIG. 11(*a*), is important, but the boundary part between the pixel array 110A and the pixel array 110B passing through the inside of the region G leads to a lack of information concerning this region G, which is not preferable. Therefore, in such a case, as shown in (b) in FIG. 11, by making the two pixel arrays 120A, 120B different in width in the long-length direction from each other, the boundary part between the pixel arrays, that is, a moving path of the dead area can be excluded from the region G Moreover, differentiating the two pixel arrays to be tiled in the width in the long-length direction from each other also has the following advantage. (a) in FIG. 12 is a view showing a state where a plurality of pixel arrays 120A that are wider in width in the long-length direction and a plurality of pixel arrays 120B that are narrower in width in the long-length direction are imposed in a silicon wafer W. (b) in FIG. 12 is a view showing a state where a plurality of pixel arrays 110 that are equal in width in the long-length direction are imposed in a silicon wafer W. As can be understood from these figures, imposing a plurality of pixel arrays 120A that are wider in long-length direction width and a plurality of pixel arrays 120B that are narrower in long-length direction width in combination results in a smaller wasted part in the silicon wafer W, and allows obtaining the pixel arrays more efficiently, than imposing a plurality of pixel arrays 110 that are equal in long-length direction width.

Here, when two substrates to form a PPS type solid-state image pickup device are arranged in the row direction of their pixel arrays in order to realize the above-described tiling method, the pixel arrays of the respective substrates being different in long-length direction width from each other result in a difference in the number of columns of the pixel arrays of the respective substrates from each other, so that a problem to be described in the following occurs.

Figure 13:
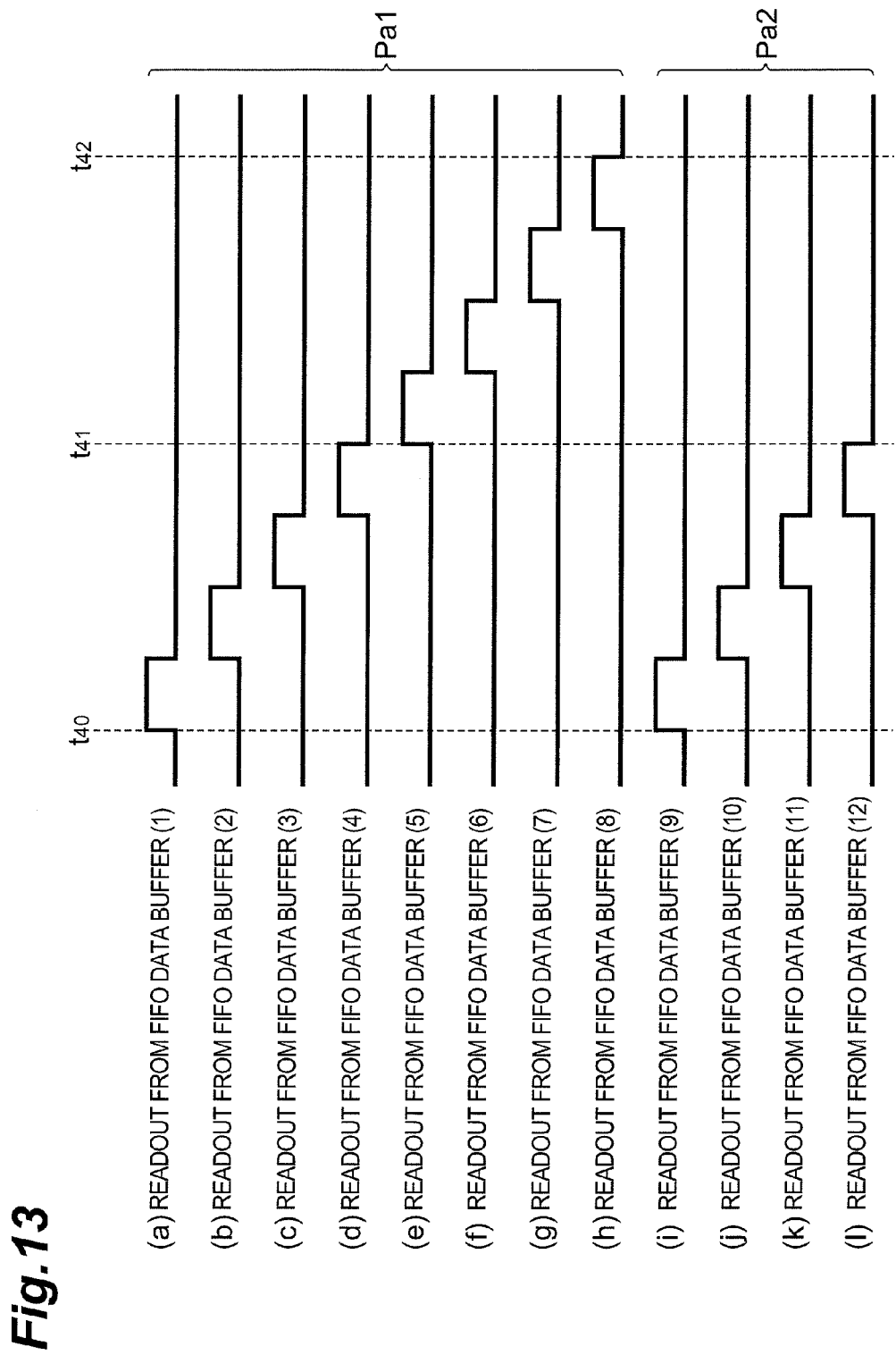
FIG. 13 is a timing chart indicating in (a) to (h) examples of the timing where digital values are output from eight FIFO data buffers (1) to (8) respectively corresponding to eight pixel blocks of one pixel array, and in (i) to (l), examples of the timing where digital values are output from four FIFO data buffers (9) to (12) respectively corresponding to four pixel blocks of the other pixel array.

Now, it is supposed that one pixel array that is wider in long-length direction width has eight pixel blocks equal in column number to each other, and the other pixel array that is narrower in long-length direction width has four pixel blocks equal in column number to each other. FIG. 13 is a timing chart indicating in (a) to (h) examples of the timing where digital values are output from eight FIFO data buffers (1) to (8) respectively corresponding to eight pixel blocks of one pixel array, and in (i) to (l), examples of the timing where digital values are output from four FIFO data buffers (9) to (12) respectively corresponding to four pixel blocks of the other pixel array. Normally, it is common that one output port Pa1 is configured by the FIFO data buffers (1) to (8) corresponding to the pixel array formed on one substrate, and another output port Pa2 is configured by the FIFO data buffers (9) to (12) corresponding to the pixel array formed on the other substrate, but in the case of such a configuration, the time required, when outputting digital values from the respective output ports Pa1, Pa2 in parallel, until all digital values are completely output is different between the output ports Pa1, Pa2. In the example shown in FIG. 13, the FIFO data buffer (1) of the output port Pa1 and the FIFO data buffer (9) of the output port Pa2 start an output operation at the time $t_{40}$, but the output port Pa1 is larger in the number of FIFO data buffers than the output port Pa2, and thus the time $t_{42}$ where the output operation of the output port Pa1 ends is later than the time $t_{41}$ where the output operation of the output port Pa2 ends. Therefore, for the time $t_{41}$ to $t_{42}$, the output port Pa2 can only be placed in a waiting state, so that the time required for imaging of one frame becomes long.

Figure 14:
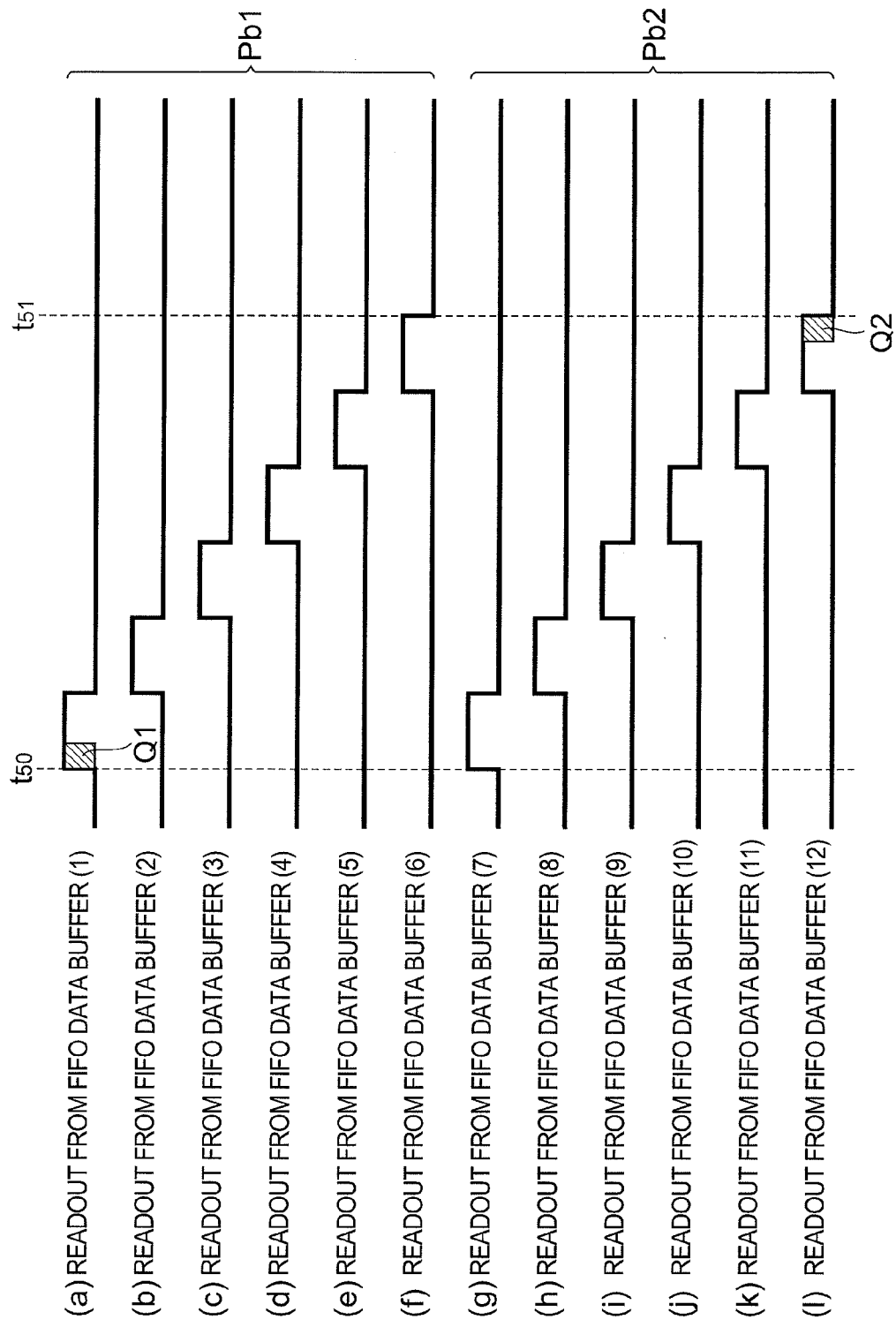
FIG. 14 is a timing chart indicating in (a) to (h) examples of the timing where digital values are output from eight FIFO data buffers (1) to (8) respectively corresponding to eight pixel blocks of one pixel array, and in (i) to (l), examples of the timing where digital values are output from four FIFO data buffers (9) to (12) respectively corresponding to four pixel blocks of the other pixel array.

Such a problem can be solved by approximating (preferably, equalizing) the number of columns (number of FIFO data buffers) of a pixel array included in one output port and the number of columns (number of FIFO data buffers) of a pixel array included in the other output port to each other. By, for example, as shown in FIG. 14, allocating six FIFO data buffers (1) to (6) on one output port Pb1, and allocating the same number of FIFO data buffers (7) to (12) on the other output port Pb2, the time required until all digital values are completely output is equalized between the output ports Pb1, Pb2. In the example shown in FIG. 14, the FIFO data buffer (1) of the output port Pb1 and the FIFO data buffer (7) of the output port Pb2 start an output operation at the time $t_{50}$, and the time $t_{51}$ where the output operation of the output port Pb1 ends is coincident with the time where the output operation of the output port Pb2 ends.

In consideration of such points, in the solid-state image pickup device 1 of the present embodiment, the FIFO data buffers 23A to 23L of the signal output section 20, when outputting digital values according to the amounts of charges generated in the respective pixels P to the data bus DB, output respectively in parallel the digital values corresponding to the respective columns on and before the n-th column (that is, from the first column to the n-th column) of the pixel array 10A from the FIFO data buffers 23A to 23F, and the digital values corresponding to the respective columns on and after the (n+1)-th column and the first column to the NB-th column of the pixel array 10B (that is, from the (n+1)-th column of the pixel array 10A through the NA-th column and the first column of the pixel array 10B to the NB-th column) from the FIFO data buffers 23G to 23L. By thus dividing an output operation at a boundary of the column (the n-th column) between the first column and the NA-th column of the pixel array 10A with a larger number of columns to output digital values in parallel, the number of columns in one divided region (region on the left side of the boundary line E in FIG. 3) and the number of columns in the other divided region (region on the right side of the boundary line E in FIG. 3) can be equalized or approximated to each other in the number of columns.

Therefore, by the solid-state image pickup device 1 according to the present embodiment, as compared to, for example, a method for outputting digital values from the first column to the NA-th column of the pixel array 10A and outputting in parallel therewith digital values from the first column to the NB-th column of the pixel array 10B, the wait time in an output operation can be approximated to zero, so that the time required for imaging of one frame can be effectively reduced.

Such an effect becomes particularly prominent when the number of columns of the first column to the n-th column in the pixel array 10A is equal to a sum of the number of columns of the (n+1)-th column to the NA-th column in the pixel array 10A and the number of columns of the first column to the NB-th column in the pixel array 10B. That is, by equalizing the number of columns in one region (region on the left side of the boundary line E in FIG. 3) divided at a boundary of the n-th column and the number of columns in the other region (region on the right side of the boundary line E in FIG. 3) to each other, the wait time in an output operation of digital values becomes almost zero, so that the time required for imaging of one frame can be more effectively reduced.

Moreover, in the solid-state image pickup device 1 according to the present embodiment, one or a plurality of consecutive columns including the first column of the pixel array 10A and one or a plurality of consecutive columns including the NB-th column of the pixel array 10B serve as a non-sensitive region shielded from incident X-rays by the X-ray shielding member 5 (refer to, for example, FIG. 4(b)). Of the digital values to be output from the signal output section 20, digital values corresponding to pixels included in this non-sensitive region result in invalid data not relevant to an X-ray image.

In such a case, if the output order of digital values in one region divided at a boundary of the n-th column and the output order of digital values in the other region are the same order, the following disadvantage occurs. That is, in FIG. 14, where invalid data caused by the X-ray shielding member 5 exists at points indicated by symbols Q1, Q2, if the output order of digital values of the respective columns is of forward order (ascending order) in both regions as in the same figure, the invalid data Q1 is output first from one port Pb1, and the invalid data Q2 is output last from the other port Pb2. If the positions of invalid data Q1, Q2 in the output order of digital values are different between the output ports Pb1, Pb2 as such, this can be a barrier when performing real-time processing in another electronic circuit.

To cope with such problems, in the solid-state image pickup device 1 according to the present embodiment, the output order of digital values in one region (region on the left side of the boundary line E in FIG. 3) divided at a boundary of the n-th column and the output order of digital values in the other region (region on the right side of the boundary line E in FIG. 3) are reverse to each other (refer to (e) to (i) in FIG. 7, (e) to (i) in FIG. 8, (b) to (g) in FIG. 9, and (b) to (g) in FIG. 10). That is, the signal output section 20 outputs digital values corresponding to the respective columns from the first column to the n-th column of the pixel array 10A, sequentially starting from the n-th column up until the first column, and outputs digital values corresponding to the respective columns from the (n+1)-th column of the pixel array 10A through the NA-th column and the first column of the pixel array 10B to the NB-th column, sequentially in a reverse order to that of the first column to the n-th column of the pixel array 10A.

Figure 15:
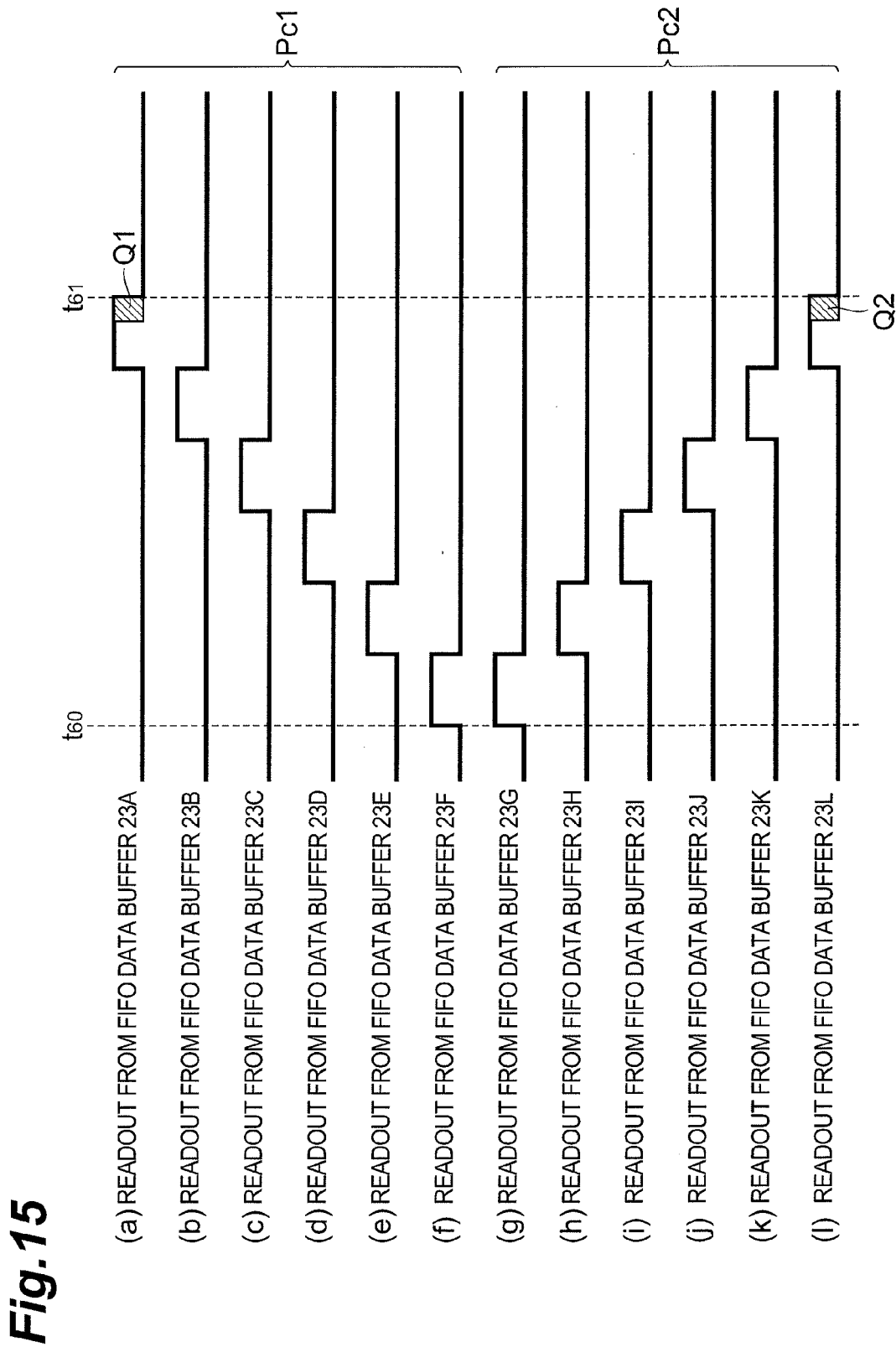
FIG. 15 is a timing chart indicating an output order of digital values from respective FIFO data buffers 23A to 23L.

FIG. 15 is a timing chart indicating an output order of such digital values from the respective FIFO data buffers 23A to 23L. (a) to (f) in FIG. 15 show output timings in the FIFO data buffers 23A to 23F, and correspond to (b) to (g) in FIG. 9. Moreover, (g) to (l) in FIG. 15 show output timings in the FIFO data buffers 23G to 23L, and correspond to (b) to (g) in FIG. 10. Referring to the figure, the FIFO data buffer 23F of the output port Pa and the FIFO data buffer 23G of the output port Pc2 start an output operation at the time $t_{60}$, and at the time $t_{61}$, the output operation of the output ports Pc1, Pc2 ends as a result of the readout from the FIFO data buffers 23A and 23L being completed. As a result of the signal output section 20 outputting digital values in such an order, the output timings of the invalid data Q1, Q2 from the respective output ports Pc1, Pc2 can be made coincident with each other, which thus allows easily performing real-time processing in another electronic circuit.

In addition, in the solid-state image pickup device 1 according to the present embodiment, tiling of the pixel arrays 10A, 10B is performed by arranging the semiconductor substrates 3A and 3B side by side, but there are provided, for example, the following tiling methods. For example, as shown in (a) in FIG. 16, the semiconductor substrates 3A, 3B vapor-deposited with film-like scintillators 4A, 4B on their surfaces, respectively, are arranged adjacent to each other on the same plane. In this method, the scintillator 4A, 4B slightly wraps around the side (edge) of the semiconductor substrate 3A, 3B, and thus the width of the dead area C is determined by a distance from the pixel P located at an endmost part of each of the pixel arrays 10A, 10B to the edge of each of the semiconductor substrates 3A, 3B, a thickness of the parts of the scintillators 4A, 4B respectively wrapped around the edges of the semiconductor substrates 3A, 3B, and a gap (clearance) secured between the semiconductor substrates 3A, 3B.

Moreover, (b) in FIG. 16 shows a method for arranging the semiconductor substrates 3A, 3B adjacent to each other on the same plane as in FIG. 16(a), but this method is different from that shown in FIG. 16(a) in that the scintillators 4A, 4B are vapor-deposited in a lump after the semiconductor substrates 3A, 3B are arranged side by side. In the method shown in FIG. 16(b), since the scintillators 4A, 4B are vapor-deposited after the semiconductor substrates 3A, 3B are arranged, the dead area C can be narrowed in width by the amount that the scintillators 4A, 4B are not wrapped around the edges of the semiconductor substrates 3A, 3B, as compared with the method shown in FIG. 16(a).

Moreover, (c) in FIG. 16 shows a method for arranging the semiconductor substrates 3A, 3B so that an end portion of the semiconductor substrate 3B is overlapped with an end portion of the semiconductor substrate 3A. In this method, it is preferable to dispose the semiconductor substrates 3A, 3B so that the pixel arrays 10A, 10B of the semiconductor substrates 3A, 3B are coincident with each other in the horizontal direction position of one end thereof. This allows extreme narrowing of the dead area C.

The solid-state image pickup device of the present invention is not limited to the above embodiment, and various other modifications can be made. For example, in the above-mentioned embodiment, the signal output section 20 outputs digital values corresponding to the respective columns from the first column to the n-th column of the pixel array 10A sequentially in reverse order, and outputs digital values corresponding to the respective columns from the (n+1)-th column of the pixel array 10A to the NB-th column of the pixel array 10B sequentially in forward order. The output orders of digital values corresponding to the respective columns of the pixel arrays 10A, 10B are not limited thereto, and it may be possible to output digital values corresponding to the respective columns from the first column to the n-th column of the pixel array 10A sequentially in forward order, and output digital values corresponding to the respective columns from the (n+1)-th column of the pixel array 10A to the NB-th column of the pixel array 10B sequentially in reverse order. In this case, the output timings of the invalid data Q1, Q2 indicated in FIG. 15 are both at the head of row-by-row data (immediately after the time $t_{60}$), but because the output timings of the invalid data Q1, Q2 from the respective output ports Pc1, Pc2 coincide with each other, the effects of the solid-state image pickup device of the present invention can be favorably obtained. Moreover, although it has been described to make data from the respective output ports flow to one data bus simultaneously, a separate data bus may be provided for each output port, or two data buses each connected to the respective output ports may be provided in parallel.

Here, in the solid-state image pickup device according to the above-described embodiment, used is a solid-state image pickup device for generating image data according to an incident X-ray image, including: a first substrate having a first pixel array formed of M×NA (M and NA are each an integer not less than 2) pixels each including a photodiode that are two-dimensionally arrayed in M rows and NA columns; a second substrate having a second pixel array formed of M×NB (NB is an integer not less than 2 and smaller than NA) pixels each including a photodiode that are two-dimensionally arrayed in M rows and NB columns, and a first column of which is arranged along an NA-th column of the first pixel array; (NA+NB) readout wiring lines disposed for each column of the first and second pixel arrays, and each connected with the photodiode included in the pixel of a corresponding column via a readout switch; a signal output section for holding a voltage value according to an amount of charge input through the readout wiring line, and outputting the held voltage value converted to a digital value by one or a plurality of analog/digital converters; and a scintillator for generating scintillation light in response to incident X-rays to convert the X-ray image into an optical image, and outputting the optical image to the first and second pixel arrays, configured such that one or a plurality of consecutive columns including a first column of the first pixel array and one or a plurality of consecutive columns including an NB-th column of the second pixel array serve as a non-sensitive region shielded from incident X-rays, the signal output section outputs the digital values corresponding to the respective columns from the first column to an n-th column ($2 \leq n < NA$) of the first pixel array, sequentially starting from the first column up until the n-th column, or starting from the n-th column up until the first column, and in parallel with this output, outputs the digital values corresponding to the respective columns from an (n+1)-th column of the first pixel array through the NA-th column and the first column of the second pixel array to the NB-th column, sequentially in a reverse order to that of the first column to the n-th column of the first pixel array.

Moreover, the above-described solid-state image pickup device may be configured such that the number of columns of the first column to the n-th column in the first pixel array is equal to a sum of the number of columns of the (n+1)-th column to the NA-th column in the first pixel array and the number of columns of the first column to the NB-th column in the second pixel array. That is, by equalizing the number of columns of one region divided at a boundary of the n-th column and the number of columns of the other region to each other, the wait time in an output operation of digital values becomes almost zero, so that the time required for imaging of one frame can be more effectively reduced.

INDUSTRIAL APPLICABILITY

The present invention can be applied as a solid-state image pickup device with a configuration of the solid-state image pickup device where pixel arrays formed on two substrates are tiled in their row direction, in which the time required for imaging of one frame is reduced.

REFERENCE SIGNS LIST

1—solid-state image pickup device, 2—base member, 3A, 3B—semiconductor substrate, 4A, 4B—scintillator, 5—X-ray shielding member, 6—control section, 10A, 10B—pixel array, 20—signal output section, 21A to 21L—signal readout section, 22A to 22L—A/D converter, 23A to 23L—FIFO data buffer, 30A, 30B—scan shift register, 31A, 31B—readout shift register, 100—X-ray imaging system, 104—swing arm, 106—X-ray generating device, 113—slide mechanism, A—subject, $A_2$—amplifier, B—moving direction, C—dead area, $C_{21}$, $C_{22}$—integrating capacitive element, $C_3$—holding capacitive element, DB—data bus, $H_1$ to $H_{NA}$, $H_1$ to $H_{NB}$—holding circuit, $L_G$—gain setting wiring line, $L_H$—hold wiring line, $L_{H,j}$—j-th column selecting wiring line, $L_{O,j}$—j-th column readout wiring line, $L_{out}$—voltage output wiring line, $L_R$—reset wiring line, $L_{V,m}$—m-th row selecting wiring line, P, $P_{m,j}$—pixel, Pa1, Pa2, Pb1, Pb2, Pc1, Pc2—output port, PD—photodiode, Q1, Q2—invalid data, Reset—reset controlling signal, $S_1$ to $S_{NA}$, $S_1$ to $S_{NB}$—integration circuit, $SW_1$—readout switch, $SW_{21}$—discharge switch, $SW_{22}$—gain setting switch, $SW_{31}$—input switch, $SW_{32}$—output switch, W—silicon wafer.

The invention claimed is:

1. A solid-state image pickup device for generating image data according to an incident X-ray image, comprising:
   a first substrate having a first pixel array with M×NA (M and NA are each an integer not less than 2) pixels each including a photodiode that are two-dimensionally arrayed in M rows and NA columns;
   a second substrate having a second pixel array with M×NB (NB is an integer not less than 2 and smaller than NA) pixels each including a photodiode that are two-dimensionally arrayed in M rows and NB columns, and a first column of which is arranged along an NA-th column of the first pixel array;
   (NA+NB) readout wiring lines disposed for each column of the first and second pixel arrays, and each connected to the photodiode included in the pixel of a corresponding column via a readout switch;
   a signal output section for holding a voltage value according to an amount of charge input through the readout wiring line, and outputting the held voltage value converted to a digital value by one or a plurality of analog/digital converters; and
   a scintillator for generating scintillation light in response to incident X-rays to convert the X-ray image into an optical image, and outputting the optical image to the first and second pixel arrays, wherein
   one or a plurality of consecutive columns including a first column of the first pixel array and one or a plurality of consecutive columns including an NB-th column of the second pixel array serve as a non-sensitive region shielded from incident X-rays, and
   the signal output section outputs the digital values corresponding to the respective columns from the first column to an n-th column ($2 \leq n < NA$) of the first pixel array, sequentially starting from the first column to the n-th column, or starting from the n-th column to the first column, and in parallel with this output, outputs the digital values corresponding to the respective columns from an (n+1)-th column of the first pixel array through the NA-th column and the first column of the second pixel array to the NB-th column, sequentially in a reverse order to that of the first column to the n-th column of the first pixel array.

2. The solid-state image pickup device according to claim 1, wherein the number of columns of the first column to the n-th column in the first pixel array is equal to a sum of the number of columns of the (n+1)-th column to the NA-th column in the first pixel array and the number of columns of the first column to the NB-th column in the second pixel array.

3. A solid-state image pickup device for generating image data according to an incident radiation image, comprising:

a first substrate having a first pixel array with M×NA (M and NA are each an integer not less than 2) pixels each including a photodiode that are two-dimensionally arrayed in M rows and NA columns;

a second substrate having a second pixel array with M×NB (NB is an integer not less than 2 and smaller than NA) pixels each including a photodiode that are two-dimensionally arrayed in M rows and NB columns, and a first column of which is arranged along an NA-th column of the first pixel array;

(NA+NB) readout wiring lines disposed for each column of the first and second pixel arrays, and each connected to the photodiode included in the pixel of a corresponding column via a readout switch; and a signal output section for holding a signal according to an amount of charge input through the readout wiring line, and outputting the held signal, wherein the signal output section outputs the signals corresponding to the respective columns from the first column to an n-th column ($2 \leqq n < NA$) of the first pixel array sequentially, and in parallel with this output, outputs the signals corresponding to the respective columns from an (n+1)-th column of the first pixel array through the NA-th column and the first column of the second pixel array to the NB-th column sequentially.

4. The solid-state image pickup device according to claim 3, wherein the radiation image is an X-ray image.

* * * * *

UNITED STATES PATENT AND TRADEMARK OFFICE
CERTIFICATE OF CORRECTION

PATENT NO.       : 8,368,028 B2                                                Page 1 of 1
APPLICATION NO.  : 12/999188
DATED            : February 5, 2013
INVENTOR(S)      : Mori et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 104 days.

Signed and Sealed this
First Day of September, 2015

Michelle K. Lee
*Director of the United States Patent and Trademark Office*